US012607561B2

(12) United States Patent
Kuhn et al.

(10) Patent No.: US 12,607,561 B2
(45) Date of Patent: Apr. 21, 2026

(54) SYSTEMS, METHODS AND ASSAYS FOR OUTLIER CLUSTERING UNSUPERVISED LEARNING AUTOMATED REPORT (OCULAR)

(71) Applicant: UNIVERSITY OF SOUTHERN CALIFORNIA, Los Angeles, CA (US)

(72) Inventors: Peter Kuhn, Los Angeles, CA (US); Carmen Ruiz Velasco, Los Angeles, CA (US); Shoujie Chai, Los Angeles, CA (US); James Hicks, Los Angeles, CA (US); Anand Ratnakar Kolatkar, Los Angeles, CA (US); Nicholas Matsumoto, Los Angeles, CA (US); Rafael Nevarez, Los Angeles, CA (US); Benjamin Ormseth, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 1012 days.

(21) Appl. No.: 17/769,253

(22) PCT Filed: Oct. 14, 2020

(86) PCT No.: PCT/US2020/055575
§ 371 (c)(1),
(2) Date: Apr. 14, 2022

(87) PCT Pub. No.: WO2021/076623
PCT Pub. Date: Apr. 22, 2021

(65) Prior Publication Data
US 2024/0125700 A1    Apr. 18, 2024

Related U.S. Application Data

(60) Provisional application No. 62/914,763, filed on Oct. 14, 2019.

(51) Int. Cl.
*G01N 21/64* (2006.01)
*G01N 33/574* (2006.01)
*G01N 33/58* (2006.01)

(52) U.S. Cl.
CPC ..... *G01N 21/6428* (2013.01); *G01N 21/6458* (2013.01); *G01N 33/57492* (2013.01); *G01N 33/582* (2013.01); *G01N 2021/6439* (2013.01); *G01N 2333/4742* (2013.01); *G01N 2333/70589* (2013.01); *G01N 2333/70596* (2013.01)

(58) Field of Classification Search
CPC ........... G01N 21/6428; G01N 21/6458; G01N 33/57492; G01N 33/582; G01N 2333/4742; G01N 2333/70589
See application file for complete search history.

(56) References Cited

U.S. PATENT DOCUMENTS

| | | | | |
|---|---|---|---|---|
| 6,025,128 A | * | 2/2000 | Veltri | G16B 40/20 |
| | | | | 436/63 |
| 6,407,395 B1 | * | 6/2002 | Perov | G01N 21/6452 |
| | | | | 250/459.1 |
| 10,692,209 B2 | | 6/2020 | Sashida | |
| 2005/0092934 A1 | * | 5/2005 | Kang | G02B 21/16 |
| | | | | 250/458.1 |
| 2005/0158804 A1 | * | 7/2005 | Yao | G01N 33/58 |
| | | | | 435/7.5 |
| 2014/0056807 A1 | * | 2/2014 | Di Vizio | G01N 1/34 |
| | | | | 435/7.1 |
| 2016/0377545 A1 | | 12/2016 | Wang | |
| 2017/0270346 A1 | | 9/2017 | Ascierto et al. | |
| 2018/0017568 A1 | | 1/2018 | Masubuchi et al. | |
| 2018/0196049 A1 | | 7/2018 | Kuhn et al. | |
| 2018/0203014 A1 | * | 7/2018 | Cheresh | C12Q 1/6886 |
| 2018/0232883 A1 | * | 8/2018 | Sethi | G16H 30/40 |
| 2018/0371552 A1 | | 12/2018 | Hsieh et al. | |
| 2020/0110090 A1 | * | 4/2020 | Davis | C07K 16/30 |
| 2020/0225234 A1 | * | 7/2020 | Kim | C12Y 601/0101 |

FOREIGN PATENT DOCUMENTS

| | | |
|---|---|---|
| CN | 108693009 A | 10/2018 |
| JP | 2018-180635 A | 11/2018 |

OTHER PUBLICATIONS

Meng (Clinical Cancer Research 2004 10:8152-8162) (Year: 2004).*
International Search Report and Written Opinion dated Jan. 28, 2021 for PCT Appn. No. PCT/US2020/055575, 14 pgs.
Lin, P.P. et al., "Comprehensive in situ co-detection of aneuploid circulating endothelial and tumor cells," Scientific Reports, 7:9789, 2017, pp. 1-10.
Preliminary Search Report dated Oct. 26, 2023 for EP Appn. No. 20876427.4 filed May 11, 2022, 11 pgs.
Office Action dated Jul. 24, 2025 for Chinese Application No. 202080086298.6, (includes translation), 23 pgs.

* cited by examiner

*Primary Examiner* — Changhwa J Cheu

(74) *Attorney, Agent, or Firm* — Brooks Kushman P.C.

(57) ABSTRACT

A system for identification of a biological structure present in a liquid biopsy sample is provided. The system identifies common biological structures and rare biological structures based on their fluorescence characteristics and morphology. The identified biological structures may be used in diagnosis and treatment of a human afflicted with a disease. Examples described in this disclosure also relate to methods and assays that may be used together with the systems of this disclosure for diagnosis and treatment of a human afflicted with a disease.

39 Claims, 25 Drawing Sheets

Patient example 1:

MDAnd54907 metastatic prostate cancer

Blood

Conventional CTC

CTC Vim+

Triple positive round cell

Platelet coated CTC

Extracellular vesicles

Patient example 1:

MDAnd54907 metastatic prostate cancer

Bone Marrow

Conventional CTC

CTC Vim+

Vim+ only

Platelet coated CTC

CTC Vim+

Cell cluster (heterogeneous cell types), CTC and CTC Vim+

Cell cluster (homogeneous cell types), CTC

Cluster of cells (heterogeneous cell types) + platelet coated CTC

Patient example 2:

SU147 stage I Non Small Cell Lung Cancer (NSCLC)

Blood

Endothelial cells CK-

Cluster of cells (homogeneous cell types), endothelial cells CK-

DAPI only cell

Double positive round cell

Patient example 3:

SU048 stage I Non Small Cell Lung Cancer (NSCLC)

Blood

Endothelial cells CK+

Endothelial cells CK-

Cluster of cells (homogeneous cell types), endothelial cells CK-

Cluster of cells (homogeneous cell types), endothelial cells CK+

DAPI only cell

Patient example 4:
VA352 prostate cancer patient
Bone Marrow

Conventional CTC

Large cell CK+

Examples of endothelial cells (red circles)/WBC (CD45+) Vim+ (White circles) and /WBC (CD45+) Vim- (blue circles).

SYSTEMS, METHODS AND ASSAYS FOR OUTLIER CLUSTERING UNSUPERVISED LEARNING AUTOMATED REPORT (OCULAR)

CROSS-REFERENCE TO RELATED APPLICATIONS

This application is the U.S. national phase of PCT Appln. No. PCT/US2020/055575 filed Oct. 14, 2020, which claims the benefit of U.S. provisional application Ser. No. 62/914,763 filed Oct. 14, 2019, the disclosure of which is hereby incorporated in its disclosures of which are hereby incorporated in their entirety by reference herein.

STATEMENT REGARDING FEDERALLY SPONSORED RESEARCH OR DEVELOPMENT

This invention was made with government support under. CA143906 awarded by the National Institutes of Health. The government has certain rights in the invention."

TECHNICAL FIELD

In at least one aspect, a system for identification of biological structures present in a liquid biopsy sample based on fluorescence characteristics and morphology of biological structures is provided. In another aspect, a method and an assay for identification of the biological structures present in a liquid biopsy sample is provided. Additional aspects further relate to diagnosis and treatment of a human afflicted with a disease by using the systems, methods and assays set forth herein.

BACKGROUND

Traditionally, the field of rare event detection in cancer (often referred to as liquid biopsy or circulating tumor cells) has focused on certain rare cell subtypes with known or presumed distinct phenotypes through various enrichment methods that select a specific target cell based on its presumably known phenotype (e.g. a protein based phenotype; a shape based phenotype; or other biophysical, physical, chemical based phenotype).

The cancer and its related cells, however, appear to be much more complex and varied than traditionally recognized, and the rare cells in the blood may not neatly fall into a specific category and/or consistent categories.

The following publications are related art for the background of this disclosure: Allard, W. J., et al., Tumor cells circulate in the peripheral blood of all major carcinomas but not in healthy subjects or patients with nonmalignant diseases. Clin Cancer Res, 2004. 10(20): p. 6897-904; Liu, C.-Y., et al., Vimentin contributes to epithelial-mesenchymal transition cancer cell mechanics by mediating cytoskeletal organization and focal adhesion maturation. Oncotarget, 2015. 6(18); Vuoriluoto, K., et al., Vimentin regulates EMT induction by Slug and oncogenic H-Ras and migration by governing Axl expression in breast cancer. Oncogene, 2011. 30(12): p. 1436-1448; Lou, X.-L., et al., Interaction between circulating cancer cells and platelets: clinical implication. Chinese journal of cancer research=Chung-kuo yen cheng yen chiu, 2015. 27(5): p. 450-460; Goubran, H. A., et al., Platelets effects on tumor growth. Semin Oncol, 2014. 41(3): p. 359-69; Li, N., Platelets in cancer metastasis: To help the "villain" to do evil. International Journal of Cancer, 2016. 138(9): p. 2078-2087; Labelle, M., S. Begum, and Richard O. Hynes, Direct Signaling between Platelets and Cancer Cells Induces an Epithelial-Mesenchymal-Like Transition and Promotes Metastasis. Cancer Cell, 2011. 20(5): p. 576-590; Boraas, L. C. and T. Ahsan, Lack of vimentin impairs endothelial differentiation of embryonic stem cells. Scientific Reports, 2016. 6: p. 30814; Miettinen, M. and J. F. Fetsch, Distribution of keratins in normal endothelial cells and a spectrum of vascular tumors: Implications in tumor diagnosis. Human Pathology, 2000. 31(9): p. 1062-1067; Dellagi, K., et al., Expression of vimentin intermediate filament cytoskeleton in acute nonlymphoblastic leukemias. Blood, 1985. 65(6): p. 1444-52; Gustmann, C., et al., Cytokeratin expression and vimentin content in large cell anaplastic lymphomas and other non-Hodgkin's lymphomas. Am J Pathol, 1991. 138(6): p. 1413-22; Satelli, A., et al., Epithelial-mesenchymal transitioned circulating tumor cells capture for detecting tumor progression. Clinical cancer research: an official journal of the American Association for Cancer Research, 2015. 21(4): p. 899-906; Yang, S. and X. Li, Recent advances in extracellular vesicles enriched with non-coding RNAs related to cancers. Genes & diseases, 2017. 5(1): p. 36-42; and Thery, C., et al., Minimal information for studies of extracellular vesicles 2018 (MISEV2018): a position statement of the International Society for Extracellular Vesicles and update of the MISEV2014 guidelines. Journal of extracellular vesicles, 2018. 7(1): p. 1535750-1535750; Zeuschner, P., J. Linxweiler, and K. Junker, Non-coding RNAs as biomarkers in liquid biopsies with a special emphasis on extracellular vesicles in urological malignancies. Expert Review of Molecular Diagnostics, 2019: p. 1-17.

Accordingly, there is a need for improved techniques in detecting and characterizing rare and common events in a liquid biopsy sample.

SUMMARY

In at least one aspect, a system for identification of a biological structure present in a liquid biopsy sample is provided. The system identifies common biological structures and rare biological structures based on their fluorescence characteristics and morphology. The identified biological structures can be used in the diagnosis and treatment of a human afflicted with a disease. Examples described in this disclosure also relate to methods and assays that may be used together with the systems of this disclosure for diagnosis and treatment of a human afflicted with a disease.

In another aspect, a system for identification of a biological structure ("biological structure identification system") present in a liquid biopsy sample is provided. This system may include an optical imaging system and a processing system. The liquid biopsy sample may include a biological structure(s). The biological structure(s) may be labeled with a fluorophore.

In another aspect, the optical imaging system may include a carrier suitable for supporting the liquid biopsy sample ("liquid biopsy sample carrier") for the identification of the biological structure(s); an illumination system capable of illuminating the liquid biopsy sample at a specific wavelength (or wavelengths); a light detection system; and a light controlling system. The light controlling system may be configured to allow detection of emitted electromagnetic radiation from the liquid biopsy sample; allow detection of electromagnetic radiation scattered by, reflected by, and/or transmitted through the liquid biopsy sample; and guide electromagnetic radiation from the illumination system to the liquid biopsy sample, and from the liquid biopsy sample to the light detection system.

In another aspect, the biological structure identification system may be configured to receive a liquid biopsy sample by using the liquid biopsy sample carrier; illuminate the liquid biopsy sample with an electromagnetic radiation that has a specific wavelength and can be absorbed by the fluorophore; detect and determine an intensity and a wavelength of fluorescence emitted by the fluorophore; generate an image of the biological structure(s); detect and determine a morphology of each biological structure using each generated image; identify type of each biological structure based on a specific morphology and a specific fluorescence wavelength of each biological structure; form a biological structure identification bucket ("identification bucket") based on the identified biological structure type, wherein each biological structure identification bucket contains the biological structure(s) that are similar in type; and form a set of identification buckets ("identification bucket set") based on the identification buckets.

In another aspect, the biological structure may be a structure with a membrane, a protein, DNA, RNA, or a combination thereof. The structure with a membrane may be a cell, a vesicle, or a combination thereof. The vesicle may be an oncosome. The oncosome may have a characteristic size (e.g. characteristic length or characteristic diameter) equal to or larger than one micrometer. The oncosome may have a characteristic size (e.g. characteristic length or characteristic diameter) larger than an exosome.

In another aspect, the liquid biopsy sample may be a non-solid biological sample. The liquid biopsy sample may be a body fluid sample. The liquid biopsy sample may include a blood sample, a bone marrow sample, a peritoneal fluid sample, a urine sample, a saliva, a vaginal fluid sample, a semen sample, a tear sample, a mucus sample, an aqueous humor sample, cerebrospinal fluid (CSF) sample, or a combination thereof. The liquid biopsy sample may include a blood sample. The liquid biopsy sample may include common immune cells and rare biological structures.

In another aspect, the rare biological structures may include cancer cells that have cancer genomic profiles and/or cancer protein markers; tumor microenvironment cells that leak into circulation, wherein these cells comprise epithelial cells, endothelial cells, mesenchymal cells, other stromal cells, cells that are in various transitional states, or a mixture thereof; immune cells that are responding to the tumor itself or cancer treatment; vesicles, or a mixture thereof. The rare biological structures may include conventional circulating tumor cells, which are CK+, vimentin−, CD31− and CD45−; circulating tumor cells, which are CK+, CD31−, CD45−, and vimentin+, and wherein tumor cells may putatively in epithelial to mesenchymal transition; tumor cells, which are CK+, and coated with platelets, which are CD31+; endothelial cells, which are CD31+, vimentin+, and CK−; endothelial cells, which are CD31+, vimentin+ and CK+; megakaryocytes, which are CD31+ and vimentin−, wherein megakaryocytes may include large cells containing a single, large, multi-lobulated, polyploidy nucleus responsible for the production of blood thrombocytes platelets; large cells, which are CD31+, and CK+, wherein these large cells may be present in the liquid biopsy samples obtained from a bone marrow; cells, which are DAPI+ and vimentin+; round cells, which are CD45+, and CK+; round cells, which are CD45+, vimentin+, and CK+; clusters of cells ("cell cluster") comprising at least two cells, wherein the cells are same type of cells and/or different types of cells; cells, which are DAPI+, CD45−, CD31−, and CK−; immune cells, which are CD45+ and vimentin−; immune cells, which are CD45+ and vimentin+(type III intermediate filament protein), extra-cellular vesicles, or a mixture thereof.

In another aspect, the liquid biopsy sample may include common biological structures and rare biological structures, wherein a total number of biological structures is a sum of number of the common biological structures and the number of rare biological structures, and wherein fraction of the rare biological structures are equal to or less than 10%, 5%, 1%, 0.1%, or 0.01% of the total number of biological structures.

In another aspect, the optical imaging system may include a fluorescence imaging system, a brightfield imaging system, or a combination thereof. The optical imaging system may include a fluorescence microscope, a brightfield microscope, or a combination thereof.

In another aspect, the emitted electromagnetic radiation may be a fluorescent radiation.

In another aspect, the processing system may include a control system, a hardware processor, a memory system, and an information conveying system.

In another aspect, the biological structure identification system may have at least one fluorescence channel. In a refinement, the biological structure identification system includes from 1 to 10 fluorescence channels. In a further refinement, the biological structure identification system includes from 4 to 7 fluorescence channels.

In another aspect, the number of fluorescence channels may be only four. These four fluorescence channels may be a first fluorescence channel configured for detection useful for nuclear segmentation and characterization; a second fluorescence channel configured to detect a cytokeratin (CK) for its epithelial-like phenotype; a third fluorescence channel configured to detect a vimentin for its endothelial/mesenchymal-like phenotype; and a fourth fluorescence channel configured to detect both a CD31 for its endothelial-like phenotype, and a CD45 for its immune cell phenotype. These four fluorescence channels may be a first fluorescence channel configured for detection of fluorescence emission at a blue color wavelength region; a second fluorescence channel configured for detection of fluorescence emission at a red color wavelength region; a third fluorescence channel configured for detection of fluorescence emission at a orange color wavelength region; and a fourth fluorescence channel configured for detection of fluorescence emission at a green color wavelength region. The first immunofluorescence channel may be configured to detect 4',6-diamidino-2-phenylindole (DAPI) for nuclear segmentation and characterization.

In another aspect, the systems of this disclosure may be configured to identify endothelial cells and immune cells from a plurality of features. Since morphology of the endothelial cells and the immune cells can be determined from the plurality of features, the endothelial cells and immune cells can also be used identify the endothelial cells and immune cells. The systems of this disclosure may be configured to identify the endothelial cells and the immune cells from the plurality of features (and/or from the morphology of the endothelial cells and the immune cells determined from the features), and to differentiate the endothelial cells from the immune cells. The endothelial cells may have more elongated morphologies as compared to the immune cells, and the immune cells may have more round morphologies as compared to the endothelial cells.

In another aspect, the morphology of the biological structure may be determined by using at least one feature of the biological structure's morphology. The morphology of the biological structure may be determined by using at least 10 features, at least 100 features, at least 500 features, or at least 1,000 features of the biological structure's morphology. The feature may be related to size, shape, texture and structure of the biological structure's morphology.

In another aspect, the liquid biopsy sample may be obtained from a diseased human. The liquid biopsy sample may be obtained from a human afflicted with a cancer.

In another aspect, the biological structure identification system may further be configured to form a disease map based on information related to the identification bucket set(s), relate this disease map to a specific disease and disease stage, and label this disease map according to the related specific disease and its stage. The biological structure identification system may further be configured to store a disease map based on information related to the identification bucket set(s) and labeled by a disease type and the disease stage, and wherein the disease may cause formation of the biological structures forming said identification bucket set(s). The biological structure identification system is configured to form disease maps of at least two different types of diseases and stages of each disease. The biological structure identification system may further be configured to form a disease atlas of disease maps based on the disease maps of different disease types and their stages.

In another aspect, the biological structure identification system may further be configured to diagnose the disease type and its stage based on the received liquid biopsy sample from a human afflicted with a disease. The biological structure identification system may further be configured to diagnose the disease type and its stage based on a liquid biopsy sample received from a human afflicted with a disease by comparing the disease map formed for the received liquid biopsy sample with the disease maps of the disease atlas stored in the biological structure identification system prior to receiving the liquid biopsy sample.

In another aspect, the biological structure identification system may further include an information conveying system. The biological structure identification system may further be configured via the information conveying system to convey to a user an information comprising an information related to types of the biological structures present in the liquid biopsy sample, the biological structure identification buckets, the disease maps, the disease atlases, or a combination thereof.

In still another aspect, an immunofluorescence assay for analyzing a liquid biopsy sample is provided. This assay may include antibodies against cytokeratin (CK), vimentin, CD31 and CD45.

In still another aspect, a method of analyzing a liquid biopsy sample is provided. This method may include having a liquid biopsy sample comprising biological structures; preparing a sample comprising a single layer of biological structures ("single layer biological structure sample") by using the liquid biopsy sample; using the assay(s) of this disclosure; staining the biological structures of the single layer biological structure sample by using four fluorescent components (e.g., dyes or components such as antibodies labeled with fluorophores); using the biological structure identification system(s) of this disclosure; identifying the rare biological structures through their fluorescence and morphology; and forming a biological structure identification bucket based on the identified biological structure type, wherein each biological structure identification bucket may contain a similar type of biological structures.

In yet another aspect, a method of diagnosing a disease afflicting a patient is provided. This method may include having a liquid biopsy sample from the patient comprising biological structures; preparing a sample comprising a single layer of biological structures ("single biological structure layer sample") by using the liquid biopsy sample; staining the biological structures of the single biological structure layer sample with an assay have four fluorescent components (e.g., dyes or components such as antibodies labeled with fluorophores); using the biological structure identification system(s) of this disclosure; identifying the rare biological structures through their fluorescence and morphology; forming a biological structure identification bucket ("identification bucket") based on the identified biological structure type, wherein each biological structure identification bucket contains the biological structure(s) that are similar in type; forming a set of identification buckets ("identification bucket set") based on the identification buckets; comparing information related to the identification bucket set to that of the atlas; determining the disease afflicting the patient; and treating the patient.

Exemplary features of the system and the method are further disclosed through the following specific aspects:

In a first specific aspect, a system for identification of a biological structure present in a liquid biopsy sample comprises:

an optical imaging system; and a processing system;

wherein the liquid biopsy sample comprises a biological structure(s), and wherein the biological structure(s) are labeled with a fluorophore;

wherein the optical imaging system comprises:

a carrier suitable for supporting the liquid biopsy sample ("liquid biopsy sample carrier") for the identification of the biological structure(s);

an illumination system capable of illuminating the liquid biopsy sample at a specific wavelength (or wavelengths);

a light detection system; and a light controlling system configured to:

allow detection of emitted electromagnetic radiation from the liquid biopsy sample;

allow detection of electromagnetic radiation scattered by, reflected by, and/or transmitted through the liquid biopsy sample; and guide electromagnetic radiation from the illumination system to the liquid biopsy sample, and from the liquid biopsy sample to the light detection system;

wherein the biological structure identification system is configured to:

receive a liquid biopsy sample by using the liquid biopsy sample carrier;

illuminate the liquid biopsy sample with an electromagnetic radiation that has a specific wavelength and can be absorbed by the fluorophore;

detect and determine an intensity and a wavelength of fluorescence emitted by the fluorophore; generate an image of the biological structure(s);

detect and determine a morphology of each biological structure using each generated image;

identify type of each biological structure based on a specific morphology and a specific fluorescence wavelength of each biological structure;

form a biological structure identification bucket ("identification bucket") based on the identified biological structure type, wherein each biological structure identification bucket contains the biological structure(s) that are similar in type; and form a set of identification buckets ("identification bucket set") based on the identification buckets.

In a second specific aspect, the system, the method, and/or the assay of any preceding or following specific aspect is such that the biological structure is a structure with a membrane, a protein, DNA, RNA, or a combination thereof.

In a third specific aspect, the system, the method, and/or the assay of any preceding or following specific aspect is such that the structure with a membrane is a cell, a vesicle, or a combination thereof.

In a fourth specific aspect, the system, the method, and/or the assay of any preceding or following specific aspect is such that the vesicle is an oncosome.

In a fifth specific aspect, the system, the method, and/or the assay of any preceding or following specific aspect is such that the vesicle is an oncosome that has a characteristic size (e.g. characteristic length or characteristic diameter) equal to or larger than one micrometer.

In a sixth specific aspect, the system, the method, and/or the assay of any preceding or following specific aspect is such that the vesicle is an oncosome that has a characteristic size (e.g. characteristic length or characteristic diameter) larger than exosome.

In a seventh specific aspect, the system, the method, and/or the assay of any preceding or following specific aspect is such that the liquid biopsy sample is a non-solid biological sample.

In an eighth specific aspect, the system, the method, and/or the assay of any preceding or following specific aspect is such that the liquid biopsy sample is a body fluid sample.

In a ninth specific aspect, the system, the method, and/or the assay of any preceding or following specific aspect is such that the liquid biopsy sample comprises a blood sample, a bone marrow sample, a peritoneal fluid sample, a urine sample, a saliva, a vaginal fluid sample, a semen sample, a tear sample, a mucus sample, an aqueous humor sample, cerebrospinal fluid (CSF) sample, or a combination thereof.

In a tenth specific aspect, the system, the method, and/or the assay of any preceding or following specific aspect is such that the liquid biopsy sample comprises a blood sample.

In an eleventh specific aspect, the system, the method, and/or the assay of any preceding or following specific aspect is such that the liquid biopsy sample comprises common immune cells and rare biological structures.

In a twelfth specific aspect, the system, the method, and/or the assay of any preceding or following specific aspect is such that the rare biological structures are:

cancer cells that have cancer genomic profiles and/or cancer protein markers;

tumor microenvironment cells that leak into circulation, wherein these cells comprise epithelial cells, endothelial cells, mesenchymal cells, other stromal cells, cells that are in various transitional states, or a mixture thereof;

immune cells that are responding to the tumor itself or cancer treatment;

vesicles, or a mixture thereof.

In a thirteenth specific aspect, the system, the method, and/or the assay of any preceding or following specific aspect is such that the rare biological structures comprise:

conventional circulating tumor cells, which are CK+, vimentin−, CD31− and CD45−;

circulating tumor cells, which are CK+, CD31−, CD45−, and vimentin+, and wherein tumor cells may putatively in epithelial to mesenchymal transition;

tumor cells, which are CK+, and coated with platelets, which are CD31+;

endothelial cells, which are CD31+, vimentin+, and CK−;

endothelial cells, which are CD31+, vimentin+ and CK+;

megakaryocytes, which are CD31+ and vimentin−, wherein megakaryocytes may comprise large cells containing a single, large, multi-lobulated, polyploidy nucleus responsible for the production of blood thrombocytes platelets;

large cells, which are CD31+ and CK+, wherein these large cells may be present in the liquid biopsy samples obtained from a bone marrow;

cells, which are DAPI+ and vimentin+;

round cells, which are CD45+ and CK+;

round cells, which are CD45+, vimentin+, and CK+;

clusters of cells ("cell cluster') comprising at least two cells, wherein the cells are same type of cells and/or different types of cells;

cells, which are DAPI+, CD45−, CD31−, and CK−;

immune cells, which are CD45+ and vimentin−;

immune cells, which are CD45+ and vimentin+(type III intermediate filament protein), extra-cellular vesicles, or a mixture thereof.

In a fourteenth specific aspect, the system, the method, and/or the assay of any preceding or following specific aspect is such that the liquid biopsy sample comprises common biological structures and rare biological structures, wherein a total number of biological structures is a sum of number of the common biological structures and the number of rare biological structures, and wherein fraction of the rare biological structures are equal to or less than 10%, 5%, 1%, 0.1%, or 0.01% of the total number of biological structures.

In a fifteenth specific aspect, the system, the method, and/or the assay of any preceding or following specific aspect is such that the optical imaging system comprises a fluorescence imaging system, a brightfield imaging system, or a combination thereof.

In a sixteenth specific aspect, the system, the method, and/or the assay of any preceding or following specific aspect is such that the emitted electromagnetic radiation is a fluorescent radiation.

In a seventeenth specific aspect, the system, the method, and/or the assay of any preceding or following specific aspect is such that the optical system comprises an excitation filter, an emission filter, a (dichroic) mirror, a lens, an optical fiber, or a combination thereof.

In an eighteenth specific aspect, the system, the method, and/or the assay of any preceding or following specific aspect is such that the optical imaging system comprises a fluorescence microscope, a brightfield microscope, or a combination thereof.

In a nineteenth specific aspect, the system, the method, and/or the assay of any preceding or following specific aspect is such that the processing system comprises a control system, a hardware processor, a memory system, and an information conveying system.

In a twentieth specific aspect, the system, the method, and/or the assay of any preceding or following specific aspect is such that the biological structure identification system has at least one fluorescence channel.

In a twenty-first specific aspect, the system, the method, and/or the assay of any preceding or following specific aspect is such that the biological structure identification system has a fluorescence channel, wherein the number of fluorescence channels is in the range of 1 to 10.

In a twenty-second specific aspect, the system, the method, and/or the assay of any preceding or following specific aspect is such that the biological structure identification system has a fluorescence channel, wherein the number of fluorescence channels is in the range of 4 to 7.

In a twenty-third specific aspect, the system, the method, and/or the assay of any preceding or following specific aspect is such that the biological structure identification system has only four fluorescence channels.

In a twenty-fourth specific aspect, the system, the method, and/or the assay of any preceding or following specific aspect is such that the biological structure identification system has only four fluorescence channels, wherein the four fluorescence channels are:

a first fluorescence channel configured for detection useful for nuclear segmentation and characterization;

a second fluorescence channel configured to detect a cytokeratin (CK) for its epithelial-like phenotype;

a third fluorescence channel configured to detect a vimentin for its endothelial/mesenchymal-like phenotype; and a fourth fluorescence channel configured to detect both a CD31 for its endothelial-like phenotype, and a CD45 for its immune cell phenotype.

In a twenty-fifth specific aspect, the system, the method, and/or the assay of any preceding or following specific aspect is such that the biological structure identification system has only four fluorescence channels, wherein the four fluorescence channels are:

a first fluorescence channel configured for detection of fluorescence emission at a blue color wavelength region;

a second fluorescence channel configured for detection of fluorescence emission at a red color wavelength region;

a third fluorescence channel configured for detection of fluorescence emission at an orange color wavelength region; and a fourth fluorescence channel configured for detection of fluorescence emission at a green color wavelength region.

In a twenty-sixth specific aspect, the system, the method, and/or the assay of any preceding or following specific aspect is such that the first immunofluorescence channel configured to detect 4',6-diamidino-2-phenylindole (DAPI) for nuclear segmentation and characterization.

In a twenty-seventh specific aspect, the system, the method, and/or the assay of any preceding or following specific aspect is such that the biological structure identification system has only four fluorescence channels, wherein the system, the method, and/or the assay are configured to identify endothelial cells and immune cells from a plurality of features. Since morphology of the endothelial cells and the immune cells can be determined from the plurality of features, the endothelial cells and immune cells can also be used identify the endothelial cells and immune cells.

In a twenty-eighth specific aspect, the system, the method, and/or the assay of any preceding or following specific aspect is such that the biological structure identification system has only four fluorescence channels, wherein the system, the method, and/or the assay are configured to identify the endothelial cells and the immune cells from a plurality of features (and/or from the morphology of the endothelial cells and the immune cells determined from the features) and to differentiate the endothelial cells from the immune cells, wherein the endothelial cells have more elongated morphologies as compared to the immune cells, and the immune cells have more round morphologies as compared to the endothelial cells.

In a twenty-ninth specific aspect, the system, the method, and/or the assay of any preceding or following specific aspect is such that the biological structure is determined by using at least one feature of the biological structure's morphology.

In a thirtieth specific aspect, the system, the method, and/or the assay of any preceding or following specific aspect is such that the morphology of the biological structure is determined by using at least 10 features, at least 100 features, at least 500 features, or at least 1,000 features of the biological structure's morphology.

In a thirty-first specific aspect, the system, the method, and/or the assay of any preceding or following specific aspect is such that the feature is related to size, shape, texture and structure of the biological structure's morphology.

In a thirty-second specific aspect, the system, the method, and/or the assay of any preceding or following specific aspect is such that the liquid biopsy sample is obtained from a diseased human.

In a thirty-third specific aspect, the system, the method, and/or the assay of any preceding or following specific aspect is such that the liquid biopsy sample is obtained from a human afflicted with a cancer.

In a thirty-fourth specific aspect, the system, the method, and/or the assay of any preceding or following specific aspect is such that the biological structure identification system is further configured to form a disease map based on information related to the identification bucket set(s), relate this disease map to a specific disease and disease stage, and label this disease map according to the related specific disease and its stage.

In a thirty-fifth specific aspect, the system, the method, and/or the assay of any preceding or following specific aspect is such that the biological structure identification system is further configured to store a disease map based on information related to the identification bucket set(s) and labeled by a disease type and the disease stage, and wherein the disease causes formation of the biological structures forming said identification bucket set(s).

In a thirty-sixth specific aspect, the system, the method, and/or the assay of any preceding or following specific aspect is such that the biological structure identification system is configured to form disease maps of at least two different types of diseases and stages of each disease.

In a thirty-seventh specific aspect, the system, the method, and/or the assay of any preceding or following specific aspect is such that the biological structure identification system is further configured to form a disease atlas of disease maps based on the disease maps of different disease types and their stages.

In a thirty-eighth specific aspect, the system, the method, and/or the assay of any preceding or following specific aspect is such that the biological structure identification system is further configured to diagnose the disease type and its stage based on the received liquid biopsy sample from a human afflicted with a disease.

In a thirty-ninth specific aspect, the system, the method, and/or the assay of any preceding or following specific aspect is such that the biological structure identification system is further configured to diagnose the disease type and its stage based on a liquid biopsy sample received from a human afflicted with a disease by comparing the disease map formed for the received liquid biopsy sample with the disease maps of the disease atlas stored in the biological structure identification system prior to receiving the liquid biopsy sample.

In a fortieth specific aspect, the system, the method, and/or the assay of any preceding or following specific aspect is such that the biological structure identification system further comprises an information conveying system; wherein the biological structure identification system is further configured to convey to a user an information comprising an information related to types of the biological structures present in the liquid biopsy sample, the biological structure identification buckets, the disease maps, the disease atlases, or a combination thereof.

In a forty-first specific aspect, an immunofluorescence assay for analyzing a liquid biopsy sample, includes antibodies against cytokeratin (CK), vimentin, CD31 and CD45.

In a forty-second specific aspect, a method of analyzing a liquid biopsy sample, comprises:

receiving a liquid biopsy sample comprising biological structures;

preparing a sample comprising a single layer of biological structures ("single layer biological structure sample") by using the liquid biopsy sample;

staining the biological structures of the single layer biological structure sample with an assay having four fluorescent dyes that each can be conjugated to an antibody specific for a protein biomarker;

using the biological structure identification system of any of the preceding or the following specific aspects identifying the rare biological structures through their fluorescence and morphology; and forming a biological structure identification bucket based on the identified biological structure type, wherein each biological structure identification bucket contains a similar type of biological structures.

In a forty-third specific aspect, a method of diagnosing a disease afflicting a patient, comprises:

receiving a liquid biopsy sample from the patient comprising biological structures;

preparing a sample comprising a single layer of biological structures ("single biological structure layer sample") by using the liquid biopsy sample;

staining the biological structures of the single biological structure layer sample with an assay having four fluorescent dyes that each can be conjugated to an antibody specific for a protein biomarker;

using the biological structure identification system of any of the preceding and the following specific aspects identifying the rare biological structures through their fluorescence and morphology;

forming a biological structure identification bucket ("identification bucket") based on the identified biological structure type, wherein each biological structure identification bucket contains the biological structure(s) that are similar in type;

forming a set of identification buckets ("identification bucket set") based on the identification buckets;

comparing information related to the identification bucket set to that of the atlas;

determining the disease afflicting the patient; and treating the patient.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The drawings are of illustrative examples. They do not illustrate all examples. Other examples may be used in addition or instead. Details that may be apparent or unnecessary may be omitted to save space or for more effective illustration. Some examples may be practiced with additional components or steps and/or without all of the components or steps that are illustrated. When the same numeral appears in different drawings, it refers to the same or like components or steps.

For a further understanding of the nature, objects, and advantages of the present disclosure, reference should be had to the following detailed description, read in conjunction with the following drawings, wherein like reference numerals denote like elements and wherein.

DETAILED DESCRIPTION

Figure 1A:
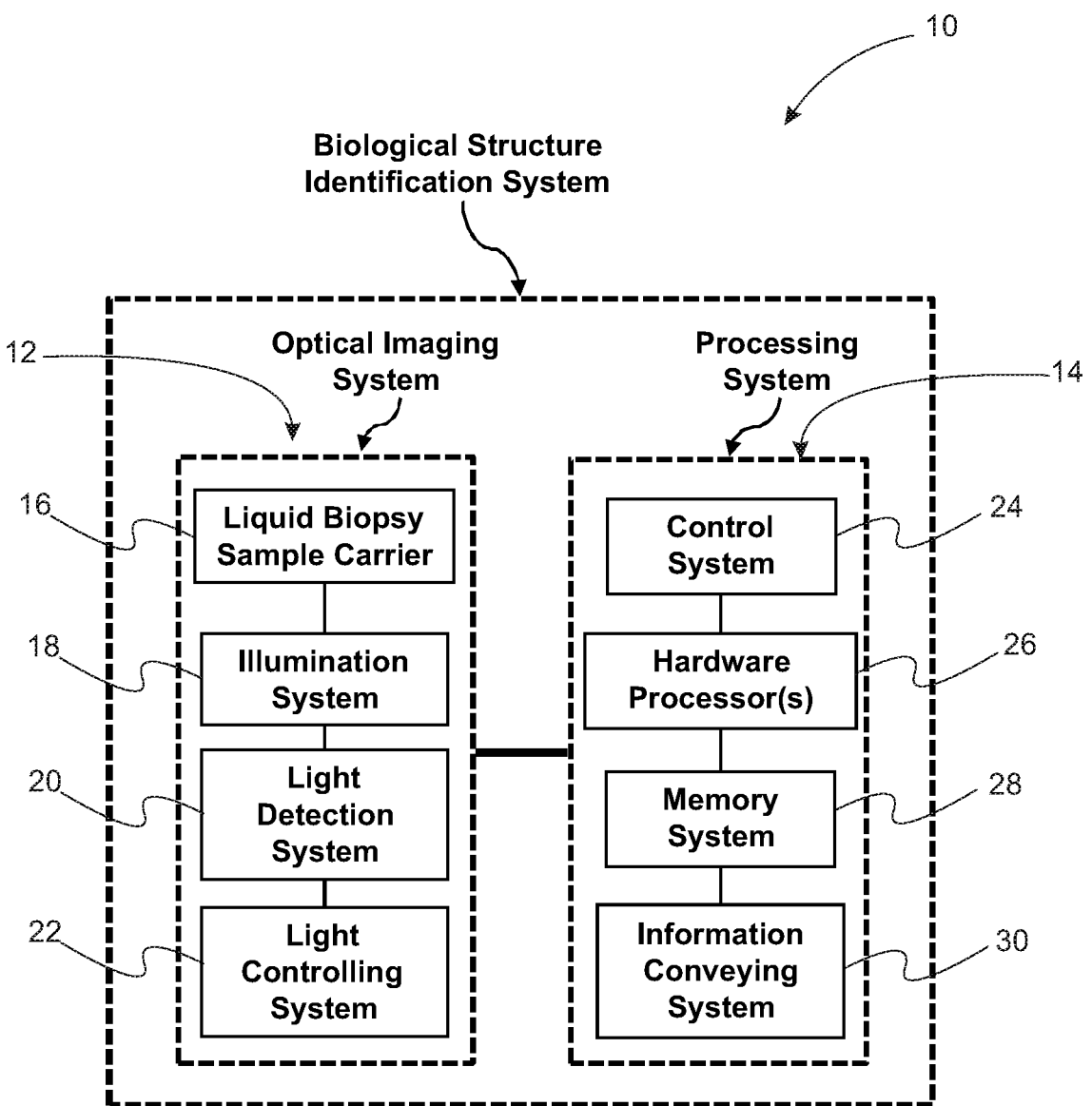
FIG. 1A. Block illustration of an exemplary biological structure identification system.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It must also be noted that, as used in the specification and the appended claims, the singular form "a," "an," and "the" comprise plural referents unless the context clearly indicates otherwise. For example, reference to a component in the singular is intended to comprise a plurality of components.

As used herein, the term "about" means that the amount or value in question may be the specific value designated or some other value in its neighborhood. Generally, the term "about" denoting a certain value is intended to denote a range within +/−5% of the value. As one example, the phrase "about 100" denotes a range of 100+/−5, i.e. the range from 95 to 105. Generally, when the term "about" is used, it can be expected that similar results or effects according to the invention can be obtained within a range of +/−5% of the indicated value.

As used herein, the term "and/or" means that either all or only one of the elements of said group may be present. For example, "A and/or B" shall mean "only A, or only B, or both A and B". In the case of "only A", the term also covers the possibility that B is absent, i.e. "only A, but not B".

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

The phrase "composed of" means "including" or "consisting of" Typically, this phrase is used to denote that an object is formed from a material.

With respect to the terms "comprising," "consisting of," and "consisting essentially of," where one of these three terms is used herein, the presently disclosed and claimed subject matter can include the use of either of the other two terms.

The term "one or more" means "at least one" and the term "at least one" means "one or more." The terms "one or more" and "at least one" include "plurality" as a subset.

The term "substantially," "generally," or "about" may be used herein to describe disclosed or claimed embodiments. The term "substantially" may modify a value or relative characteristic disclosed or claimed in the present disclosure. In such instances, "substantially" may signify that the value or relative characteristic it modifies is within ±0%, 0.1%, 0.5%, 1%, 2%, 3%, 4%, 5% or 10% of the value or relative characteristic.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1. to 2.1 the following numbers 1.2, 1.3, 1.4, 1.5, 1.6, 1.7, 1.8, 1.9, and 2.0 can be selected as lower or upper limits.

In the examples set forth herein, concentrations, temperature, measurement conditions, and reaction conditions (e.g., pressure, pH, temperature, etc.) can be practiced with plus or minus 50 percent of the values indicated rounded to or truncated to two significant figures of the value provided in the examples. In a refinement, concentrations, temperature, and reaction conditions (e.g., pressure, pH, temperature, etc.) can be practiced with plus or minus 30 percent of the values indicated rounded to or truncated to two significant figures of the value provided in the examples. In another refinement, concentrations, temperature, and reaction conditions (e.g., pressure, pH, temperature, etc.) can be practiced with plus or minus 10 percent of the values indicated rounded to or truncated to two significant figures of the value provided in the examples.

In this disclosure, the indefinite article "a" and phrases "one or more" and "at least one" are synonymous and mean "at least one".

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

The term "event" refers to the detection of an observable imaging signal and in particular to the detection of a fluorescence signal.

The term "feature" refers to any measurable parameter that characterizes an event, image, or image data. For example, features can includes shape parameters, location parameters, texture parameters, and parameters quantifying the fluorescent image.

The term "cluster" refers to a group of similar data points. In a refinement, data points can be grouped together based on the proximity of the data points to a measure of central tendency of the cluster. For example, the measure of central tendency may be the arithmetic mean of the cluster. In such an example, the data points are joined together based on their proximity to the average value in the cluster. (e.g., hierarchical clustering).

The term "similar" when referring to data points means that the data points can be placed in the same cluster. That is, similar data points can be placed or included within the same cluster after a clustering analysis. In a refinement, a cell (or other biological structure) is similar to another cell (or other biological structure) if the cell (or other biological structure) belongs in the same cluster after cluster analysis (hierarchical clustering), which is an algorithm that groups similar objects into groups. OCULAR applies a Principle Component Analysis onto the high dimensional dataset and then undergoes hierarchical clustering on the distance matrix of the PCA dataset. The output of the hierarchical algorithm determines which cells (or other biological structures) are similar to another by determining which cluster each cell belongs in. In another refinement, a set of cellular features (e.g., biological structures) is similar to another set of cellular features if the distance of the principal components between those sets is within the 1 percentile of all distances found in the distance matrix of a large dataset, which includes those sets, that underwent PCA.

The term "computing device" refers generally to any device that can perform at least one function, including communicating with another computing device.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

Throughout this application, where publications, patents, or published patent applications are referenced, the disclosures of these publications, patents, or published patent applications in their entireties are hereby incorporated by reference into this application to more fully describe the state of the art to which this invention pertains.

ABBREVIATIONS AND ACRONYMS

+: positive, when associated with a marker (e.g. CD31+, CD45+, CK+, vimentin+) or a chemical molecule (e.g. DAPI+), the cell or biological formation expresses this marker or a chemical molecule.

−: negative, when associated with a marker (e.g. CD31−, CD45−, CK−, vimentin−) or a chemical molecule (e.g. DAPI−), the cell or biological formation does not express this marker or a chemical molecule.

AF488: Alexa Fluor 488.

AF555: Alexa Fluor 555.

AF647: Alexa Fluor 647.

CD31: platelet endothelial cell adhesion molecule−1.

CD45: leukocyte-common antigen.

CTC: circulating tumor cell

CDRE: circulating rare event

CK: cytokeratin.

DAPI: 4',6-diamidino-2-phenylindole.

HD-SCA: High Definition Single Cell Assay.

OCULAR: Outlier Clustering Unsupervised Learning Automated Report.

PCA: principal component analysis.

TRITC: tetramethylrhodamine.

In general, a system for identification of a biological structure present in a liquid biopsy sample and related methods are provided. The system identifies common biological structures and rare biological structures based on their fluorescence characteristics and morphology. The identified biological structures may be used in diagnosis and treatment of a human afflicted with a disease. Examples described in this disclosure also relate to methods and assays that may be used together with the systems of this disclosure for diagnosis and treatment of a human afflicted with a disease.

Figure 1B:
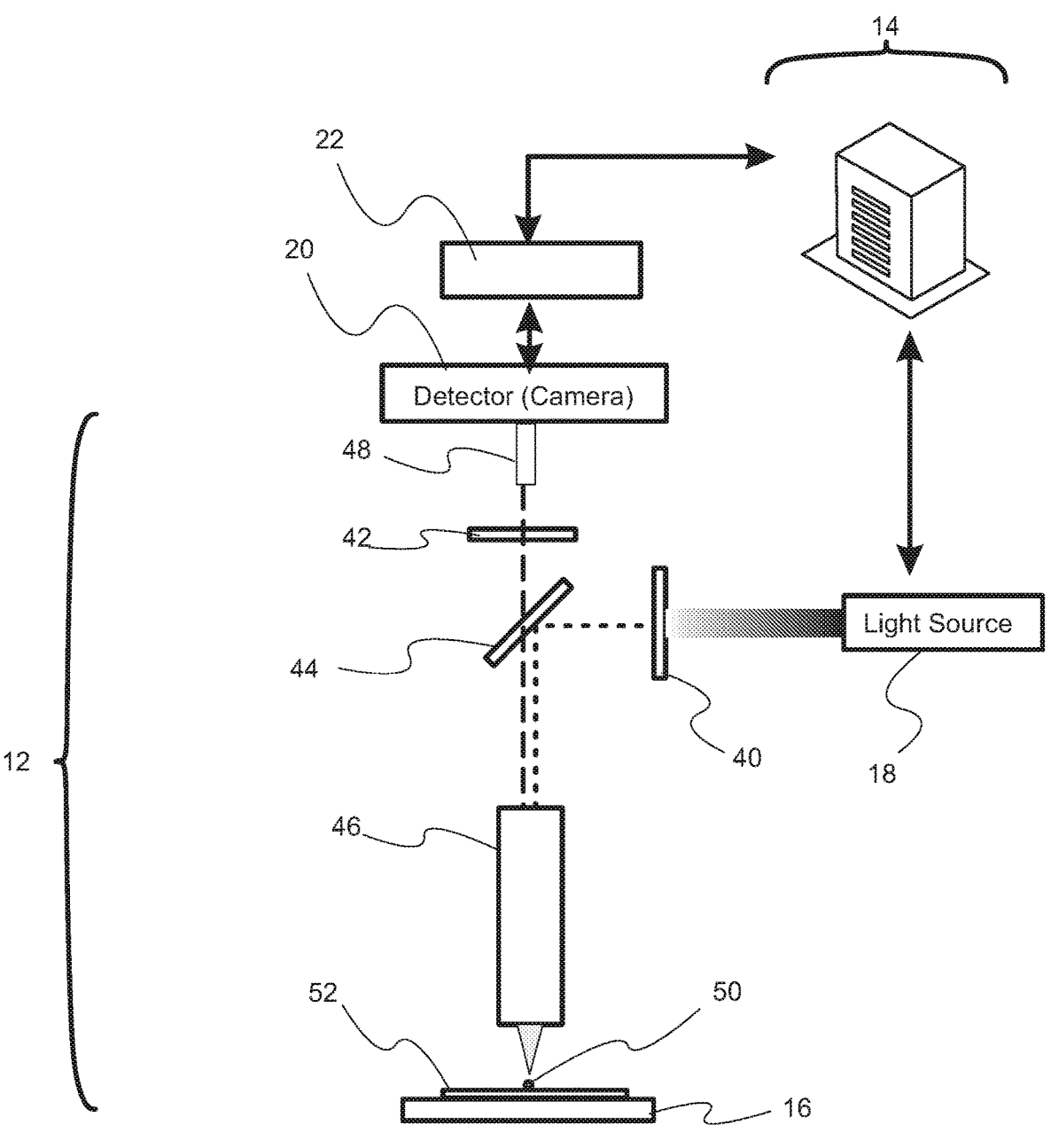
FIG. 1B. Schematic illustration of an exemplary biological structure identification system.

Referring to FIGS. 1A and 1B, an example of a system for identification of a biological structure present in a liquid biopsy sample is provided. Biological structure identification system 10 includes an optical imaging system 12 and a processing system 14. The liquid biopsy sample typically includes one or more biological structures that may be labeled with a fluorophore. Characteristically, optical imaging system 12 is configured to illuminate a liquid biopsy sample having one or more biological structures that are labeled with a fluorophore and to detect emitted electromagnetic radiation from the liquid biopsy sample as image data. Processing system 14 is configured to generate images of the at least one biology structure from the image data, detect and determine a plurality of features from the images or the image data, and form biological structure identification buckets from the plurality of features. Each biological structure identification bucket identifies biological structures that are similar in type. In a particularly useful variation, biological structure identification bucket identifies cells (as the biological structure). Typically, processing system 14 is or includes a computing device.

In a variation, the one or more biological structures include one or more rare biological structures. In a refinement, the one or more biological structures include a simultaneously identified multiple biological structures.

Still referring to FIGS. 1A and 1B, the optical imaging system 12 can include a liquid biopsy sample carrier 16 suitable for supporting the liquid biopsy sample for the identification of the biological structure(s); an illumination system 18 capable of illuminating the liquid biopsy sample at a specific wavelength or wavelengths that can be absorbed by the fluorophore; a light detection system 20 configured to detect and determine an intensity and a wavelength of fluorescence emitted by the fluorophore; and a light controlling system 22. The light controlling system 22 can be configured to allow detection of emitted electromagnetic radiation from the liquid biopsy sample; allow detection of electromagnetic radiation scattered by, reflected by, and/or transmitted through the liquid biopsy sample; and guide electromagnetic radiation from the illumination system to the liquid biopsy sample, and from the liquid biopsy sample to the light detection system. Also depicted if FIG. 1B, optical system 22 may include an optical component selected from the group consisting of an excitation filter 40, an emission filter 42, a (dichroic) mirror 44, a lens 46, an optical fiber 48, and combinations thereof. FIG. 1B also shows specimen 50 positioned on glass slide 52. In a refinement, light from an illumination system 18 (e.g., a laser light source) is passed through excitation filter 40 and then to dichroic mirror 44 which directs the excitation light through lens 46 (e.g., an objective lens). Lens 46 focusses the light onto specimen 50. The resulting emitted or scattered light passes through lens 46, dichroic mirror 44, and emission filter 42. The fluorescent light is then detected by light detection system 20 optionally through fiberoptic 48.

Still referring to FIG. 1, the processing system 14 may include a control system 24, a hardware processor 26 (e.g., CPU), a memory system 28, and an information conveying system 30. Processing system 14 will execute the analysis step via hardware processor 26. Control system 24 is the executing software components that a user uses to control and interact with the optical imaging system 12 and to initiate analysis and image construction from the image data received from the optical imaging system. The information conveying system 30 is configured to convey to a user information comprising an information related to types of the biological structures present in the liquid biopsy sample, the biological structure identification buckets, the disease maps, the disease atlases, or a combination thereof. Control system 24 and information conveying system 30 function via program codes executing on hardware processor 26 and via software and data stored in memory system 28

In a variation, the biological structure identification system 10 is configured to receive a liquid biopsy sample by using the liquid biopsy sample carrier 16 and illuminate the liquid biopsy sample with an electromagnetic radiation from illumination system 18 that has a specific wavelength or wavelengths that can be absorbed by the fluorophore. Light detection system 20 is configured to detect and determine an intensity and a wavelength of fluorescence emitted by the fluorophore with light detection system 20 or produce input data for these characteristics so that they can be determined by processing system 12.

Processing system 14 is configured to generate an image of the biological structure(s) from image data received from light detection system 20; detect and determine a morphology of each biological structure from the image and/or the image data using the plurality of features; identify the type of each biological structure based on the features defined herein (which can determine a specific morphology) of each biological structure; form a biological structure identification buckets ("identification bucket") based on the identified biological structure type such that each biological structure identification bucket contains the biological structure(s) that are similar in type and in particular cells containing such biological structure(s); and optionally, form a set of identification buckets ("identification bucket set") based on the identification buckets. In a particularly useful variation, the biological structures are cells that a placed in the identification buckets and in the identification bucket set. In this context, "placed in" means that an association between the cells (or other biological structures) and the identification buckets and in the identification bucket set is saved in computer readable form as set forth below.

Figure 2:
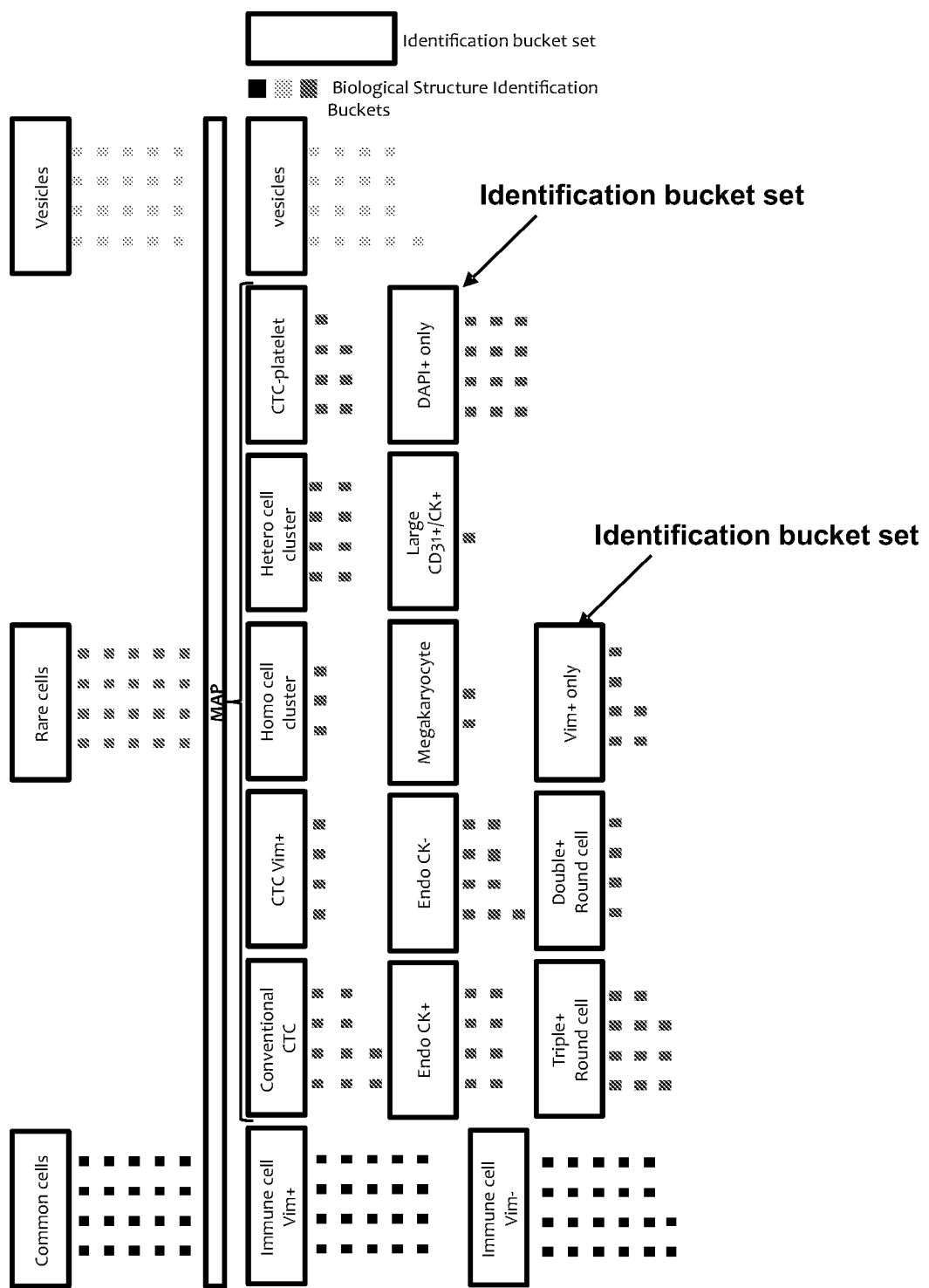
FIG. 2. Illustration of an exemplary identification map comprising identification bucket sets and identification buckets.

FIG. 2 illustrates exemplary identification buckets and identification bucket sets. From this figure, identification bucket sets are construct from a plurality of identification buckets. In this figure the identification buckets are identified by smaller squares that are color coded to provide a representation of the number of cells in a bucket. For example, the black buckets under common cells represent a high number of cells (or biological structures) in these buckets. The buckets and bucket sets can be associated with any label that is convenient for the user. It should be appreciated that the identification buckets and identification bucket sets are typically stored in a computer readable medium and in particular a non-transitory computer readable medium (e.g., random access memory, CDROM, DVD, hard drive, etc.). In a refinement, identification buckets and identification bucket sets are stored in a computer readable medium as a data structure with relationship between the stored values. Examples of data structures that can be used include, but are not limited to arrays, linked lists, records, a graph, a tree data structure (e.g., a binary tree), a data frame, a database (e.g., a relational database), and combinations thereof.

In a variation, processing system 14 is further configured to form a disease map based on information related to the biological structure identification bucket set(s), relate the disease map to a specific disease and disease stage, and label the disease map according to an identified related specific disease and disease stage.

In some aspects, the morphology of the biological structure may be determined by using at least one feature extracted from the image or image data. Typically, the image data will includes features (e.g., parameters) of the fluorescent light emitted from the sample. These features can be extracted from the generated image or the image data by using know software packages such as the EBImage which is an open source R package distributed as part of the Bioconductor project. The morphology of the biological structure may be determined by using at least 10 features, at least 100 features, at least 500 features, or at least 1,000 features extracted from the image or image data. Features can includes shape parameters, location parameters, texture parameters, and parameters quantifying the fluorescent image (e.g., specific fluorescence wavelength(s), fluorescence signal intensity, etc.). The feature may be related to size, shape, texture and structure of the biological structure's morphology. In some variations, an image mask is deployed limiting the observable image area to regions encompassed by the mask. Table 1 provides non-limiting examples of features that can be used in the analysis. Any combination of the features in Table 1 can be used.

characteristic size (e.g. characteristic length or characteristic diameter) equal to or larger than one micrometer. The oncosome may have a characteristic size (e.g. characteristic length or characteristic diameter) larger than an exosome.

In other aspects, the liquid biopsy sample may be a non-solid biological sample. The liquid biopsy sample may be a body fluid sample. The liquid biopsy sample may include a blood sample, a bone marrow sample, a peritoneal fluid sample, a urine sample, a saliva, a vaginal fluid sample, a semen sample, a tear sample, a mucus sample, an aqueous humor sample, cerebrospinal fluid (CSF) sample, or a combination thereof. The liquid biopsy sample may include a blood sample. The liquid biopsy sample may include common immune cells and rare biological structures.

In still other aspects, the rare biological structures may include cancer cells that have cancer genomic profiles and/or cancer protein markers; tumor microenvironment cells that leak into circulation, wherein these cells comprise epithelial cells, endothelial cells, mesenchymal cells, other stromal cells, cells that are in various transitional states, or a mixture

TABLE 1

| List of parameters (i.e., features) pulled from the mask and image data with the mask. | | | |
| --- | --- | --- | --- |
| Basic parameters | Moment parameters of Cell Mask and Nucleus mask | Shape parameters of Cell Mask and Nucleus mask | Haralick Parameters using the Gray Level Co-occurrence Matrix |
| Mean Intensity | cell x position within ROI | Area | Angular second moment |
| Standtard Deviation of pixel Intensity | cell y position within ROI | perimeter | contrast |
| Median absolute intensity | Major axis | Mean radius | Correlation |
| 1%, percentile intensity | Eccentricity | Standard deviation of radius of Mask | Variance |
| 5%, percentile intensity | Theta | Minimum radius | Inverse difference moment |
| 5O % percentile intensity | | Maximum radius | Sum average |
| 95% percentile intensity | | | Sum variance |
| 99% percentile intensity | | | Sum entropy |
| | | | Entropy |
| | | | Variance difference |
| | | | Entropy Difference |
| | | | Correlation measures |

In some refinements, the identification bucket may be a specific repository (e.g., classification) where information related to a specific biological structure(s) identified in a liquid biopsy sample is stored, wherein the specific biological structures may have substantially similar properties, including substantially similar morphologies and substantially similar marker profiles. The information related to the specific biological structure may be any information related to the biological structure, including the identification bucket's label, number of the specific biological structures identified in a given portion of the liquid biopsy sample analyzed, properties associated with the specific biological structure, information related to the liquid biopsy sample, the like, or a combination thereof. This information related to the specific biological structure(s) may be stored in any convenient manner. For example, the information related to the specific identification bucket may be stored in the memory system. In some refinement, the bucket is a cluster as described below.

In some aspects, at least a subset of the biological structure can a structure with a membrane, a protein, DNA, RNA, or a combination thereof. The structure with a membrane may be a cell, a vesicle, or a combination thereof. The vesicle may be an oncosome. The oncosome may have a thereof; immune cells that are responding to the tumor itself or cancer treatment; vesicles, or a mixture thereof. The rare biological structures may include conventional circulating tumor cells, which are CK+, vimentin−, CD31− and CD45−; circulating tumor cells, which are CK+, CD31−, CD45−, and vimentin+, and wherein tumor cells may putatively in epithelial to mesenchymal transition; tumor cells, which are CK+, and coated with platelets, which are CD31+; endothelial cells, which are CD31+, vimentin+, and CK−; endothelial cells, which are CD31+, vimentin+ and CK+; megakaryocytes, which are CD31+ and vimentin−, wherein megakaryocytes may comprise large cells containing a single, large, multi-lobulated, polyploidy nucleus responsible for the production of blood thrombocytes platelets; large cells, which are CD31+, and cytokeratins, which are CK+, wherein these large cells may be present in the liquid biopsy samples obtained from a bone marrow; cells, which are DAPI+ and vimentin+; round cells, which are CD45+ and CK+; round cells, which are CD45+, vimentin+, CD45+, and CK+; clusters of cells ("cell cluster') comprising at least two cells, wherein the cells are same type of cells and/or different types of cells; cells, which are DAPI+, CD45−, CD31−, and CK−; immune cells, which are CD45+ and vimentin−; immune cells, which are CD45+ and vimentin+(type III intermediate filament protein), extra-cellular vesicles, or a mixture thereof.

In some aspects, the liquid biopsy sample may include common biological structures and rare biological structures, wherein a total number of biological structures is a sum of number of the common biological structures and the number of rare biological structures, and wherein fraction of the rare biological structures are equal to or less than 10%, 5%, 1%, 0.1%, or 0.01% of the total number of biological structures.

In a refinement, the optical imaging system includes a fluorescence imaging system, a brightfield imaging system, or a combination thereof. The optical imaging system may include a fluorescence microscope, a brightfield microscope, or a combination thereof.

In some aspects, the emitted electromagnetic radiation may be a fluorescent radiation.

In some aspects, the biological structure identification system includes at least one fluorescence channel. The number of fluorescence channels may be in the range of 1 to 10, or in the range of 4 to 7. In a refinement, the number of fluorescence channels may be only four. These four fluorescence channels may be a first fluorescence channel configured for detection useful for nuclear segmentation and characterization; a second fluorescence channel configured to detect a cytokeratin (CK) for its epithelial-like phenotype; a third fluorescence channel configured to detect a vimentin for its endothelial/mesenchymal-like phenotype; and a fourth fluorescence channel configured to detect both a CD31 for its endothelial-like phenotype, and a CD45 for its immune cell phenotype. These four fluorescence channels may be a first fluorescence channel configured for detection of fluorescence emission at a blue color wavelength region; a second fluorescence channel configured for detection of fluorescence emission at a red color wavelength region; a third fluorescence channel configured for detection of fluorescence emission at an orange color wavelength region; and a fourth fluorescence channel configured for detection of fluorescence emission at a green color wavelength region. For example, these for regions can be defined by an emission filter centered at 455 nm with a bandwidth of 50 nm for blue color wavelengths, an emission filter centered at 525 nm with a bandwidth of 36 nm for green color wavelengths, an emission filter centered at 605 nm with a bandwidth of 52 nm for orange color wavelengths, and an emission filter centered at 705 nm with a bandwidth of 72 nm for red color wavelengths. The first immunofluorescence channel may be configured to detect 4',6-diamidino-2-phenylindole (DAPI) for nuclear segmentation and characterization.

In some aspects, the systems of this disclosure may be configured to identify endothelial cells and immune cells from the features and/or the morphology of the endothelial cells and the immune cells determined from the features. In particular, the system can be configured to identify the endothelial cells and the immune cells from the features (and/or morphology of the endothelial cells and the immune cells determined from the features), and to differentiate the endothelial cells from the immune cells. The endothelial cells may have more elongated morphologies as compared to the immune cells, and the immune cells may have more round morphologies as compared to the endothelial cells. In a refinement, such morphologies are determined from the features as described herein.

In some aspects, the liquid biopsy sample is obtained from a diseased human. The liquid biopsy sample may be obtained from a human afflicted with a cancer.

In some refinements, the biological structure identification system is further configured to form a disease map based on information related to the identification bucket set(s), relate this disease map to a specific disease and disease stage, and label this disease map according to the related specific disease and its stage. The biological structure identification system may further be configured to store a disease map based on information related to the identification bucket set(s) and labeled by a disease type and the disease stage, and wherein the disease may cause formation of the biological structures forming said identification bucket set(s). The biological structure identification system is configured to form disease maps of at least two different types of diseases and stages of each disease.

The biological structure identification system may further be configured to form a disease atlas ("ATLAS) of disease maps based on the disease maps of different disease types and their stages. In this regard, the atlas built by using the trillions of cellular data, performing a PCA on the dataset and then selecting the cells that would create a dataset that would have a non-overlapping region in that PCA dataspace. Each cell would represent a certain region of that space such that any subsequently scanned cell would necessarily belong to a cell in the atlas. A cell would be assigned an ATLAS cell ID by applying the ATLAS PCA transform and finding the closest ATLAS cell. For example, identifying clusters into which a cell from a patient belongs can be used to assist in disease identification, disease state, and prognosis. In this context, "belong" means that the cell (or other biological structure) has feature values representative of the cluster (e.g., within the parameter or feature boundaries of the cluster). In some refinements, the atlas and/or the disease maps in atlas include metadata such as patients identification, clinical parameters, image parameters and the like. The atlas and/or the disease maps can include this data for each cell (or other biological structures) contained therein. In a refinement, the disease atlas is stored in a computer readable medium and in particular a non-transitory computer readable medium (e.g., random access memory, CDROM, DVD, hard drive, etc.). In a refinement, the disease atlas is stored in a computer readable medium as a data structure with relationship between the stored values. Examples of data structures that can be used include, but are not limited to arrays, linked lists, records, a graph, a tree data structure (e.g., a binary tree), a database (e.g., a relational database), and combinations thereof. In a refinement, the disease atlas is stored as a database and in particular, a relational database that can be queried.

In some refinements, the biological structure identification system is further configured to diagnose the disease type and its stage based on the received liquid biopsy sample from a human afflicted with a disease. The biological structure identification system may further be configured to diagnose the disease type and its stage based on a liquid biopsy sample received from a human afflicted with a disease by comparing the disease map formed for the received liquid biopsy sample with the disease maps of the disease atlas stored in the biological structure identification system prior to receiving the liquid biopsy sample.

In a variation, an immunofluorescence assay for analyzing a liquid biopsy sample is provided. This assay may include antibodies against cytokeratin (CK), vimentin, CD31 and CD45. In a refinement, at least a subset of the antibodies against cytokeratin (CK), vimentin, CD31 and CD45 are labeled with a fluorophore. In the Baseline assay, each of cytokeratin (CK) and vimentin are independently labeled with a fluorophore while one or both of CD31 and CD45 are labeled with a fluorophore. Examples of fluorophores includes but are not limited to, DAPI and Hoechst 33342 and 33258 (as nuclear dyes), Alexa Fluor 488 (for Vimentin), Alexa Fluor 555 (for cytokeratin), Alexa Fluor 647 (for CD31/CD45), and the like.

Figure 3:
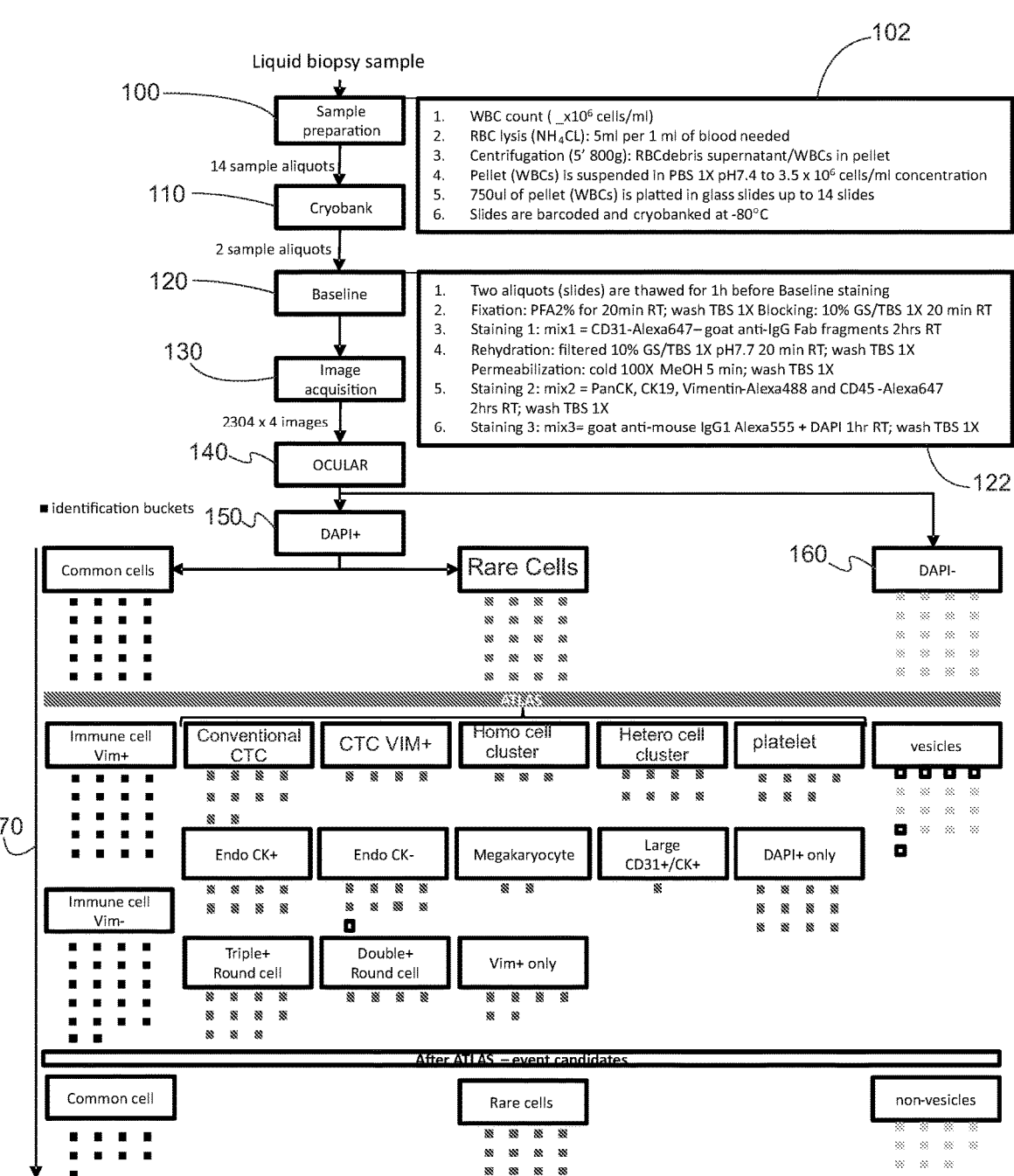
FIG. 3. Illustration of an exemplary biological structure identification method.
Figure 4:
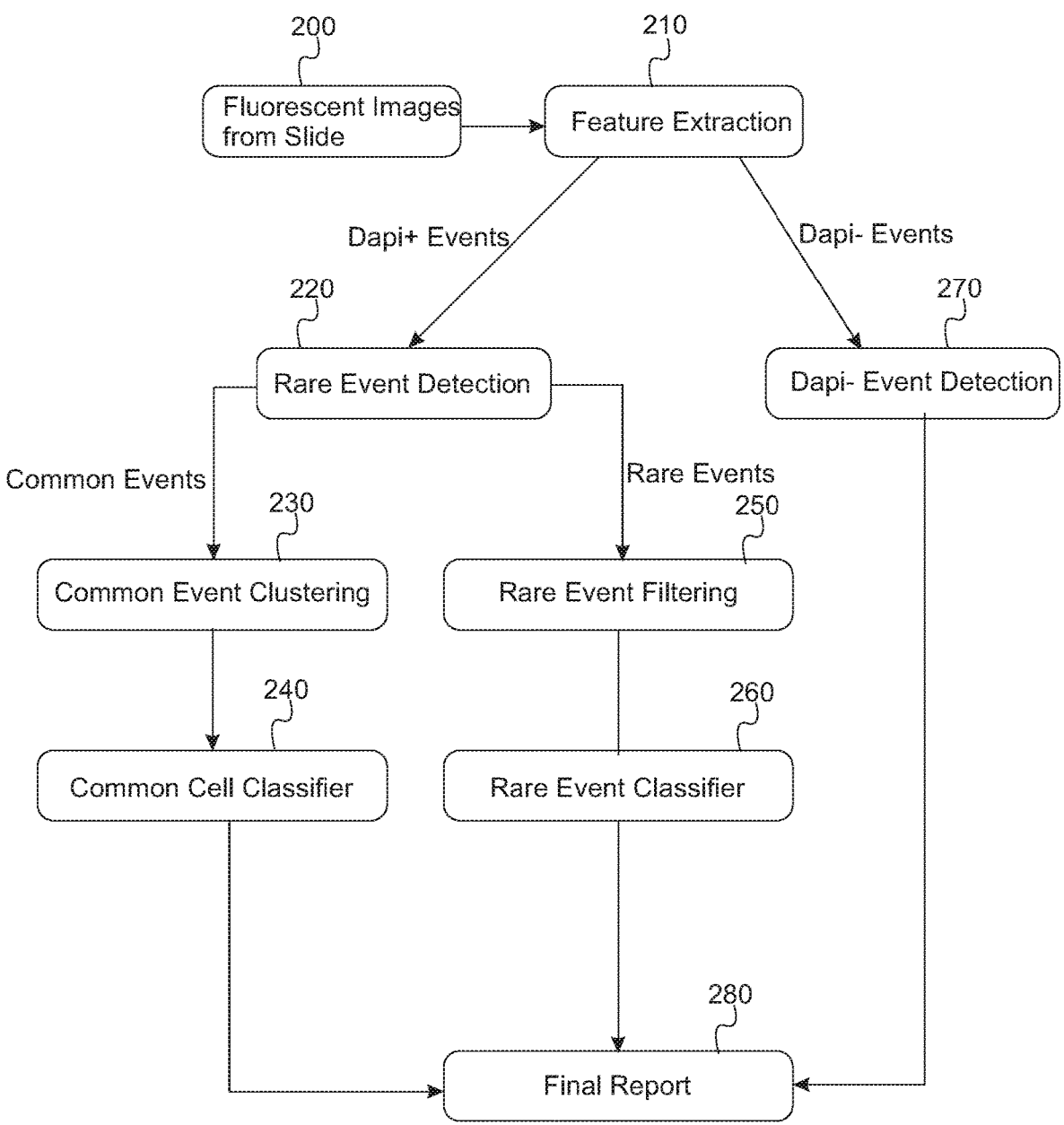
FIG. 4. Illustration of an exemplary biological structure identification method.

In a variation, a method of analyzing a liquid biopsy sample is provided. This method may include having a liquid biopsy sample comprising biological structures; preparing a sample comprising a single layer of biological structures ("single layer biological structure sample") by using the liquid biopsy sample; staining the biological structures of the single layer biological structure sample with the fluorescent assay(s) set forth herein (having four fluorescent dyes) or any fluorescent assay; using the biological structure identification system(s) of this disclosure; identifying the rare biological structures through their fluorescence and morphology; and forming a biological structure identification bucket based on the identified biological structure type, wherein each biological structure identification bucket may contain a similar type of biological structures. FIGS. 3 and 4 provide exemplary liquid biopsy sample analysis methods.

Referring to FIG. 3, a flow chart of the sample analyst method is provided. As depicted in Box 100 the liquid biopsy sample is processed in accordance to a predetermined protocol. Box 102 provide an example of such a protocol. In a refinement as depicted in box 110, sample aliquots are optionally stored in a cryobank. In the next step (Box 120), a fluorescence assay is used to stain the liquid biopsy sample (e.g., an immunofluorescence assay such as the Baseline assay (see below) or any fluorescence assay). Box 122 provides a specific example of this processing. The image data is then acquired as shown in box 130. In box 140, the acquired image data is then analyzed. The Ocular analysis protocols described below in more detail can be applied for this analysis. As part of the analysis, the image data can then be segregated into DAPI+(box 150) or DAPI- (Box 160) regions. Each region are subjected to cluster analysis as set forth below to identify bucket for classify the cells.

Referring to FIG. 4, a flow chart of an exemplary liquid biopsy sample analysis method is provided. Typically, this analysis is implement by processing system 14 or another computing device. As depicted in box 200, fluorescent images are received as an input to processing system 14. As part of the analysis nuclear and/or cell masks are generated and features extracted (e.g., over 700 features pulled from the 4 fluorescent images). As depicted by box 210, rare event detection proceeds as follows. For each region on the slide, the data tor each event will undergo dimensional reduction, and then will be hierarchical clustered into multiple groups. The number of clusters are determined by how large the dataset is. For each frame (region) on the slide, we divide the total number of cells within the region by 30 and round the number to an integer which is the number of clusters that the multidimensional data would cluster into. Rare events are defined as 1) events within the smallest population clusters and 2. events with the clusters that are most deviant from the median value of all features from all events. Rarity within a region on the slide is defined via cluster analysis. After the region undergoes feature extraction and hierarchical clustering on principal components, the clusters are sorted by 2 quantifiable measures: 1) population size in ascending order and 2) the Euclidean distance of the cluster's mean feature of all cells within the cluster to the median feature of all cells of the whole region in descending order. Clusters that are towards the top of these two lists are considered rarer than the clusters towards the bottom of the lists. In a refinement, rare events are below a predetermined rarity threshold. In a further refinement, the rare events are below a rarity threshold of 1.5%. The rarity threshold is the percentage of cells within a region on the slide of which the algorithm will define as rare. The rarity threshold is applied after sorting the clusters with the above measures. The rarity threshold is a value that can be passed into the algorithm by defining it as an argument. Separately with the two sorted lists of clusters, the algorithm will add up the rarer clusters until the total number of cells cross the rarity threshold. After performing this step with the two rare lists, the algorithm returns the unique list of cells that are within such clusters. These are the rare cell candidates within the region of the slide. Rarity within the slide is performed by a filtering method of using common cell clusters throughout all the regions of the slide and removing all rare cell candidates that are similar to any such common cell cluster. Similarity in this case is determined by the PCA dataset of both rare cell candidates and common cell cluster features. After performing a distance matrix of the combined PCA dataset, the value of the 1 percentile of all distances found in the matrix will be the maximum distance necessary to be considered similar. If a rare cell candidate is within that value of any common cell cluster, that rare cell candidate will not be labeled as rare and will add onto the respective common cell cluster that was most similar to that rare cell candidate. Each region will collect up to a certain user defined percentage of rarity of the total cells within the region. The rare event features are individually collected and sent through the rare event pipelines as rare event candidates. Each rare event includes the position of the event on the slide. In another refinement, rare biological structures (e.g., cells) are biological structure that are identified as being below a predetermined percentage of the total amount of biological structures identified. In a refinement, this predetermined percentage is in increasing order of preference, 5%, 4%, 3%, 2%, 1.5% or 1% of the total number of identified biological structures. The common events are aggregated into their respective common event cluster as a mean of the features of the events within the cluster. They are sent through the common event pipeline in this aggregated form.

As depicted by box 230, common event clustering is analyzed as follows. Since the common clusters from the previous step are determined by a single region on the slide, each common cluster is then clustered together by their similarity. The sum of those events are preserved as the data converges with one another. As depicted by box 240, a common cell classifier is applied as follows. A dataset of all known events of the assay being used (referred to as "ATLAS) is applied to each common event cluster. In particular, each common event cluster is compared to all "ATLAS" data points and classified as one of our determined cell types. These events can then be enumerated. As depicted by box 250, the rare events undergo a filtering process, where each rare event candidate is compared to each common event cluster. This cleans the rare event candidate list for slide wide rarity, instead of regional rarity. As depicted by box 260, a rare cell classifier is applied as follows. The "ATLAS" dataset of all known events of the assay is applied. Each rare event candidate will be compared to all "ATLAS" data points and classified as one of our determined cell types. This step further filters out events that are "common." The classified events can then be enumerated as certain cell types. Any event that is not classified within the "ATLAS" undergoes clustering and the aggregate information is collected and sent to the final report. As depicted by box 270, Dapi- event clustering proceed as follows. All Dapi- events from the slide are collected, undergo dimensional reduction, and the hierarchical clustered into multiple groups. Each Dapi– group has the mean of the features of the events within the cluster. Each Dapi– event data is preserved as well as their position on the slide. The aggregated cluster information is sent to the report. As depicted by box 280, each common event cluster is represented in the report as 10 montages of sample events within the cluster as well as the count of all events within that cluster and their information. Each non-classified rare event clusters is represented similarly 10 sample montages, the count of events within the cluster, and their respective aggregate information. If the user wants to retrieve the individual event data or the events within a certain cluster, the user will send a command to the server to individually montage each event within the respective cluster. Similar to the non-classified rare events, the Dapi– event clusters are represented with 10 sample montages. the count of events within the cluster, and their respective aggregate information. Ii the user wants to retrieve the individual event data for the events within a certain duster, the user will send a command to the server to individually montage each event within the respective cluster. The classified rare events, as well as any event within a cluster that the user sent to the server for individual event data collection, are individually montaged, easily sortable and Queryable, and in a user interface that can give the user a holistic view oi all rare events within the slide.

Figure 5:
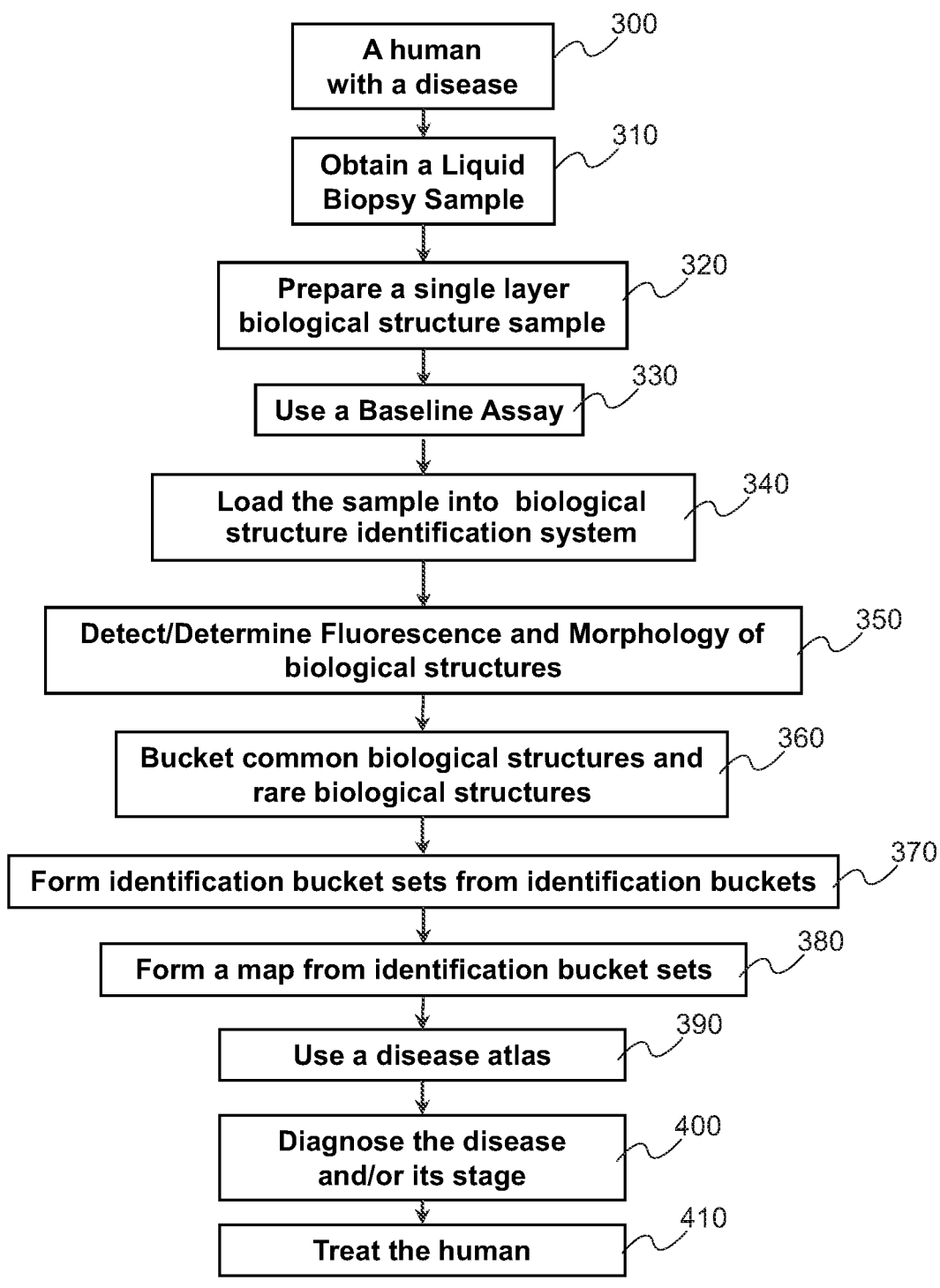
FIG. 5. Illustration of an exemplary method, for a biological structure identification, diagnosis and treatment of a patient.
Figure 6:
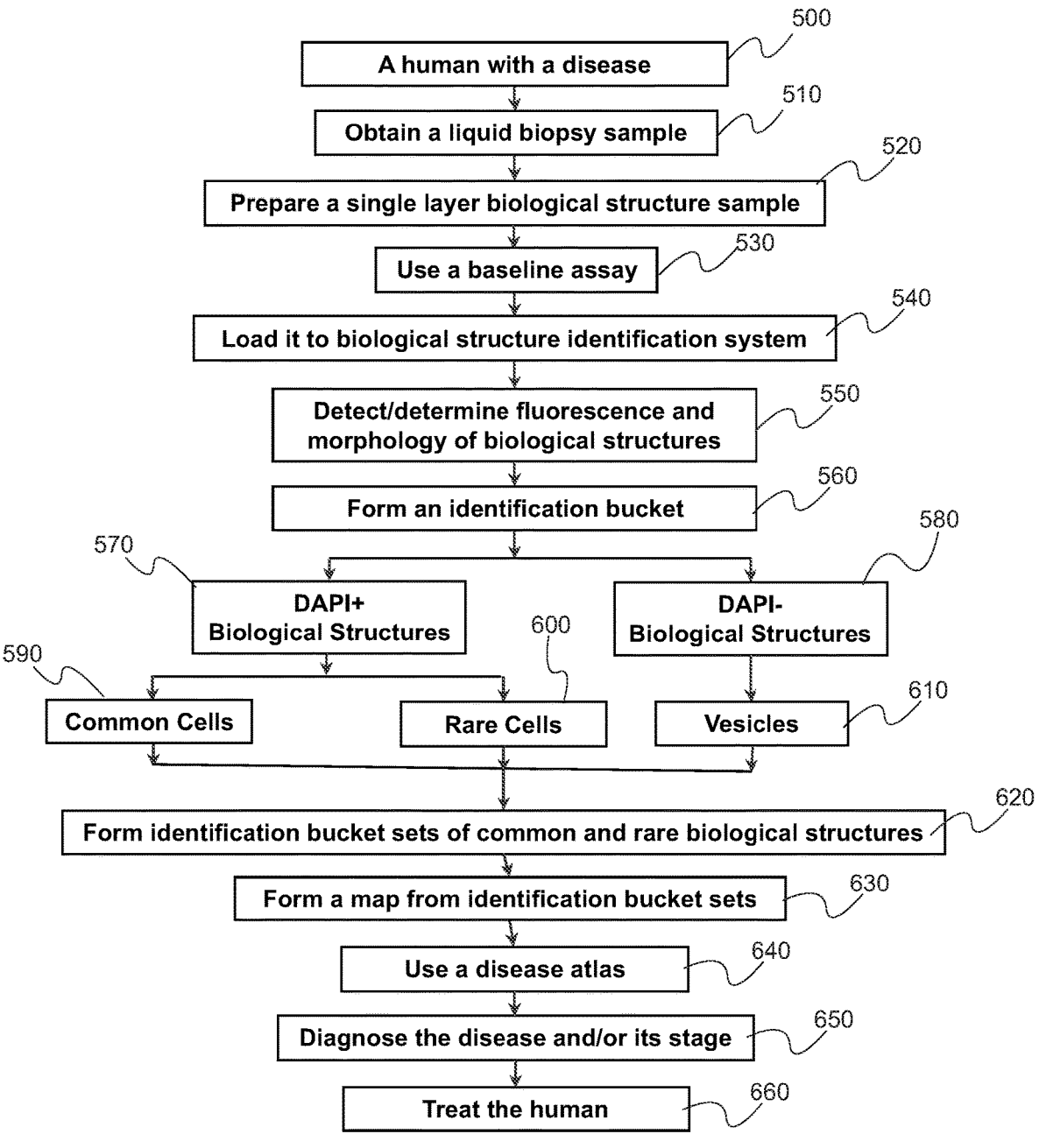
FIG. 6. Illustration of an exemplary method, for a biological structure identification, diagnosis and treatment of a patient.
Figure 7:
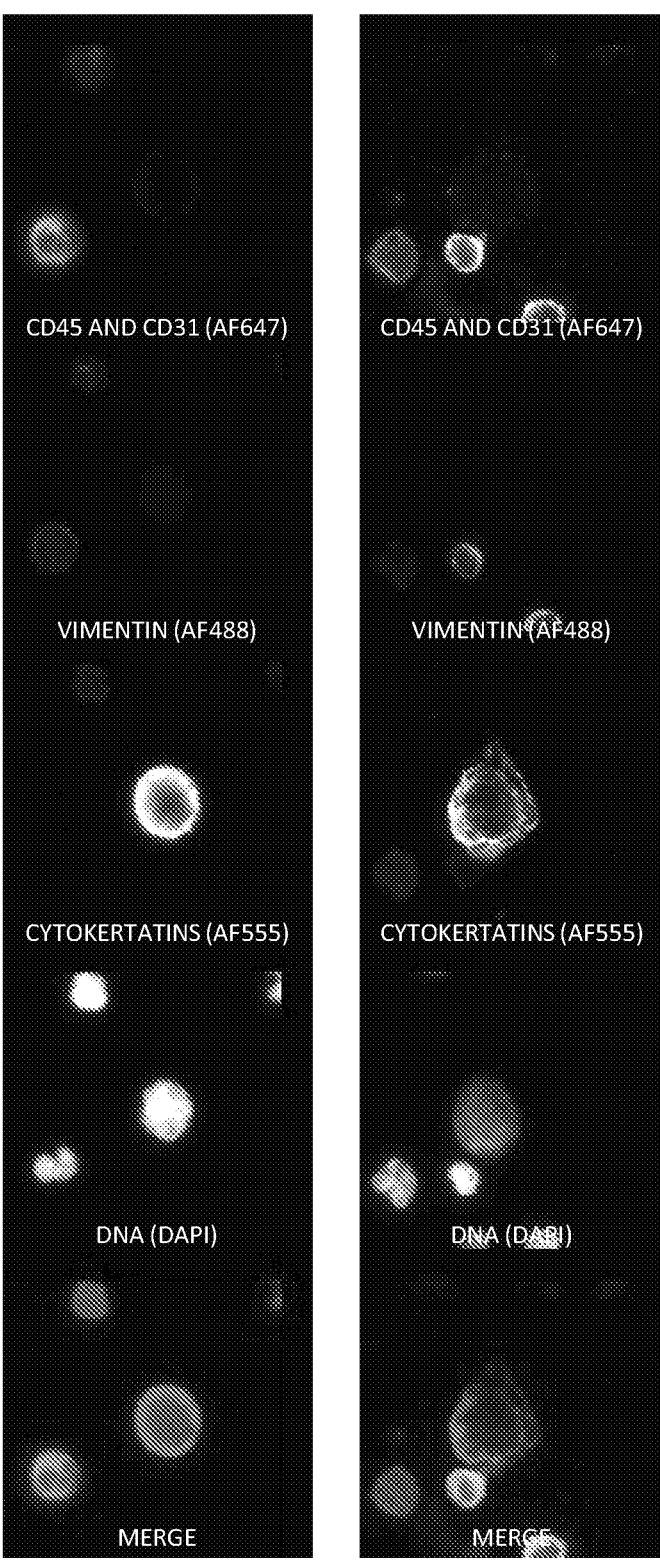
FIG. 7. Conventional circulating tumor cells (CK+/vimentin−/CD31−/CD45−).
Figure 8:
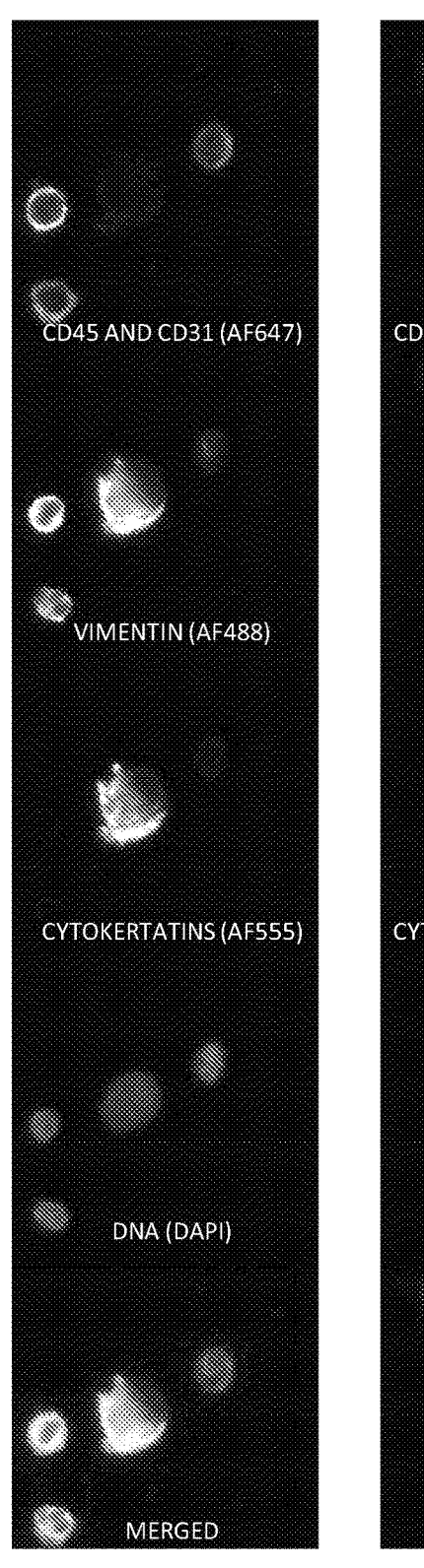
FIG. 8. Circulating tumor cells (CK+/CD31−/CD45−) that do express vimentin. Cancer cell in epithelial to mesenchymal transition.
Figure 8:
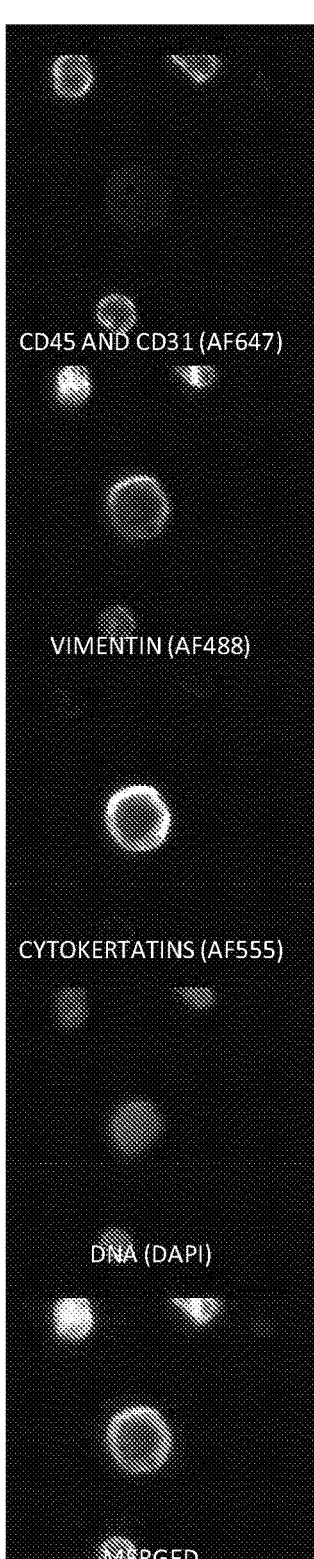
Figure 9:
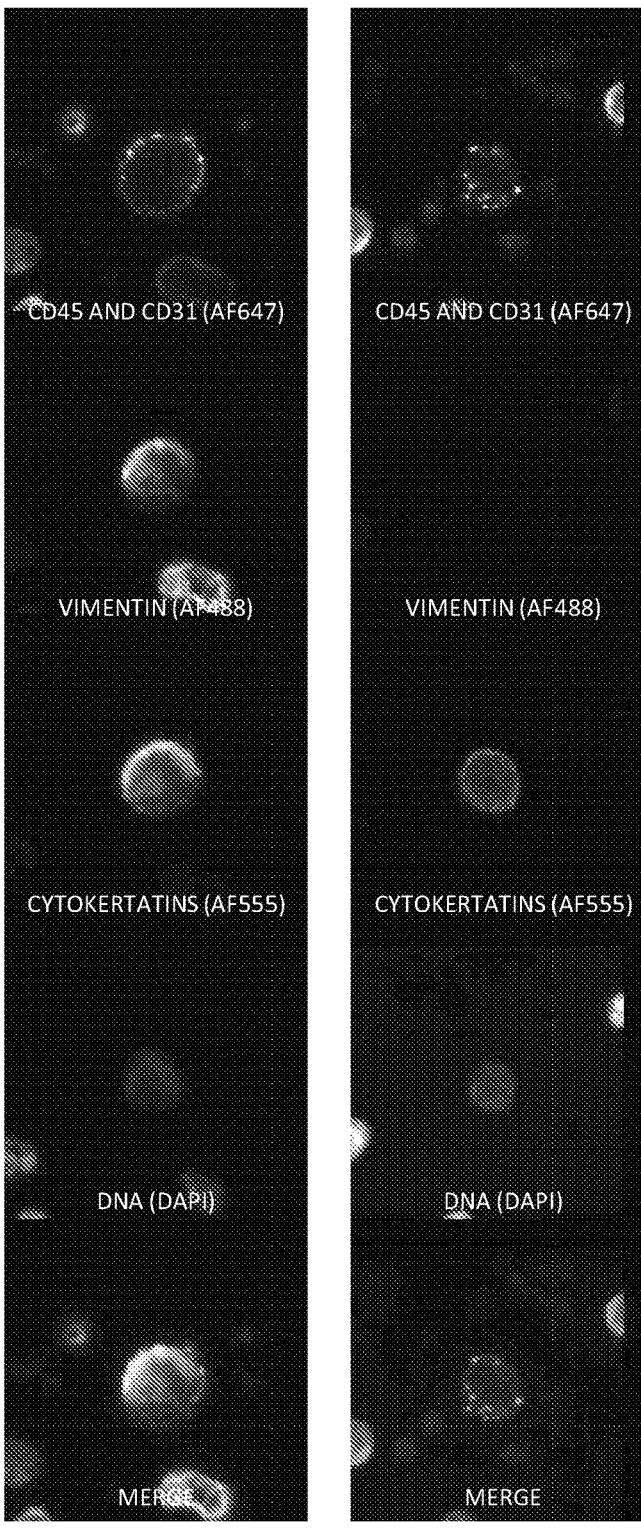
FIG. 9. Cancer cells (CK+) coated with platelets (CD31+).
Figure 10:
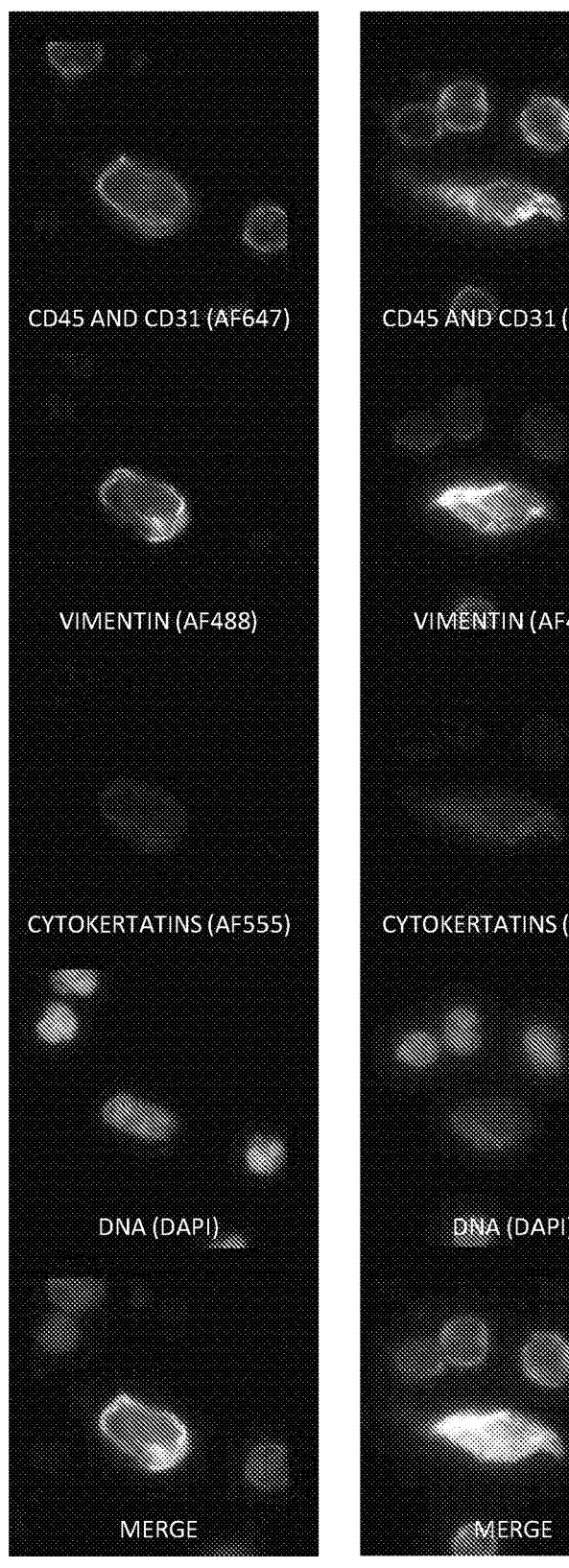
FIG. 10. Endothelial cells (CD31+/vimentin+) that do not express CK.
Figure 11:
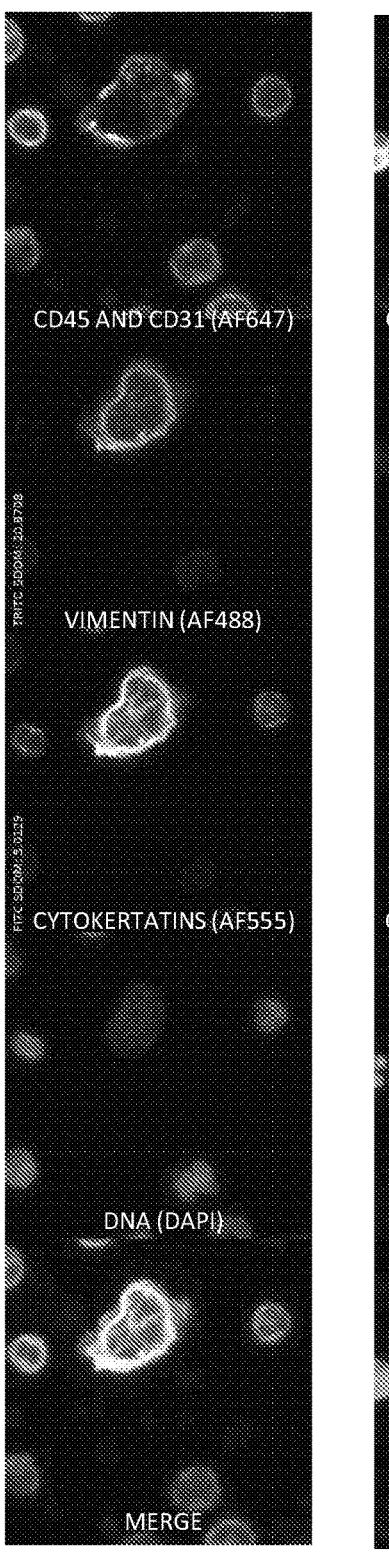
FIG. 11. Endothelial cells (CD31+/vimentin+) that express CK.
Figure 11:
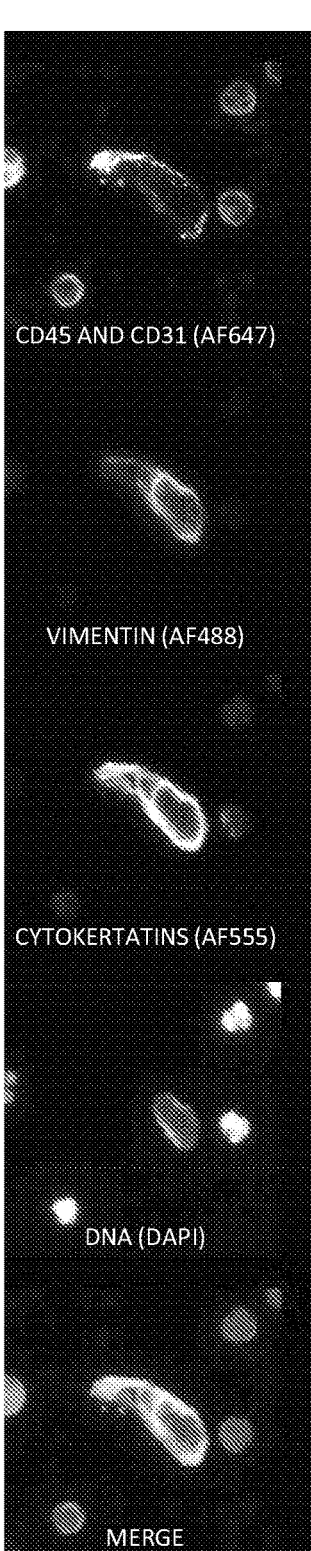
Figure 12:
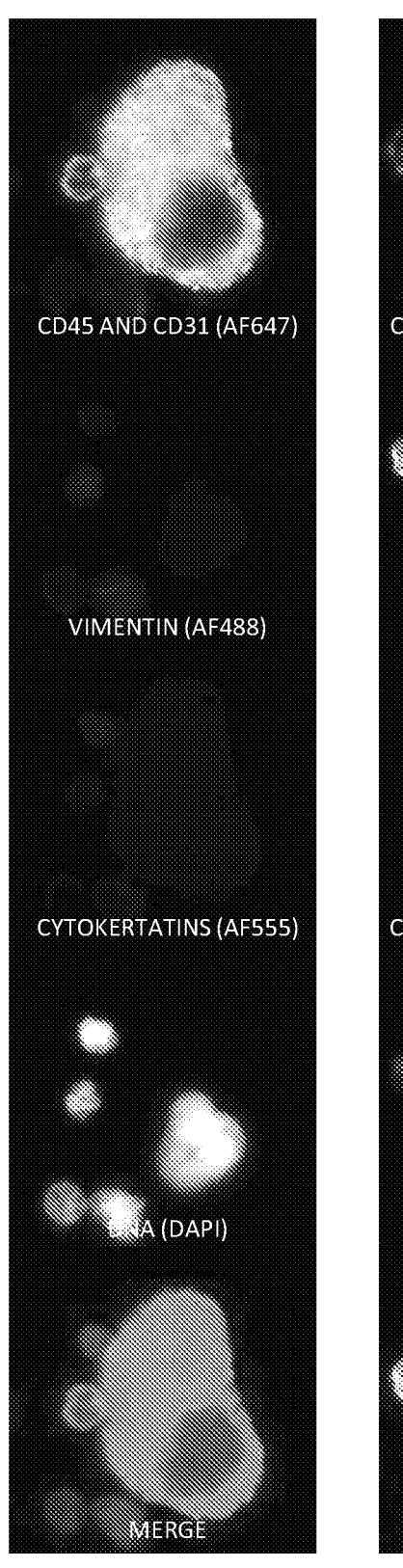
FIG. 12. Megakaryocytes (CD31+) that do not express vimentin. Large cell containing a single, large, multilobulated, polyploidy nucleus responsible for the production of blood thrombocytes platelets.
Figure 12:
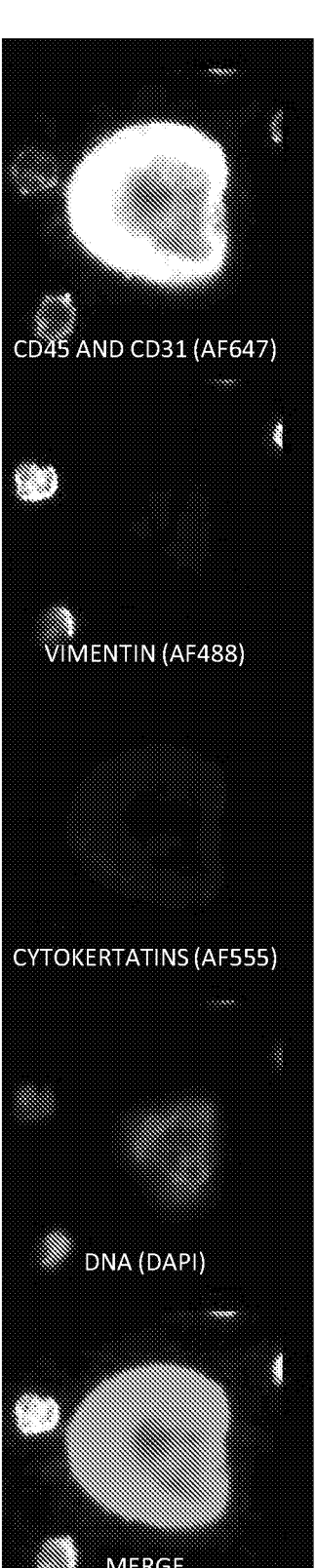
Figure 13:
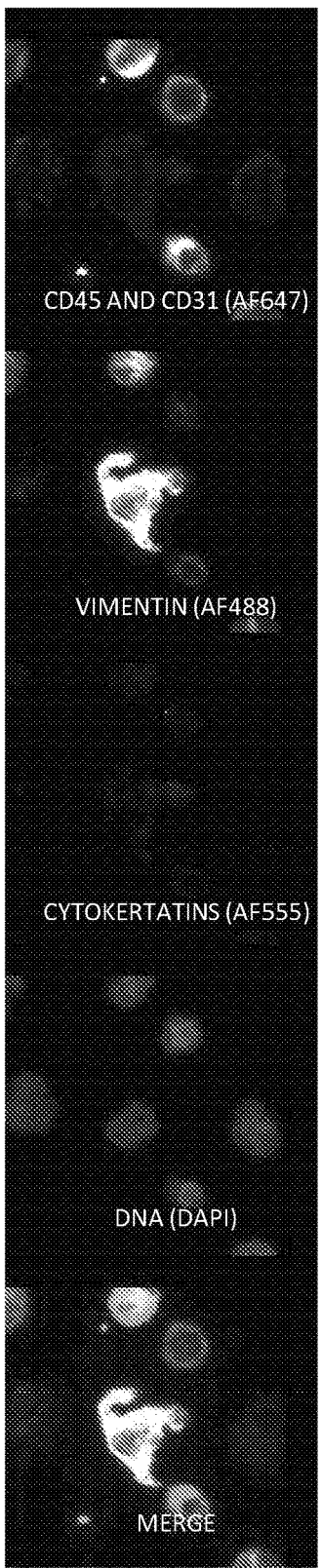
FIG. 13. Cells (DAPI+) expressing only vimentin.
Figure 13:
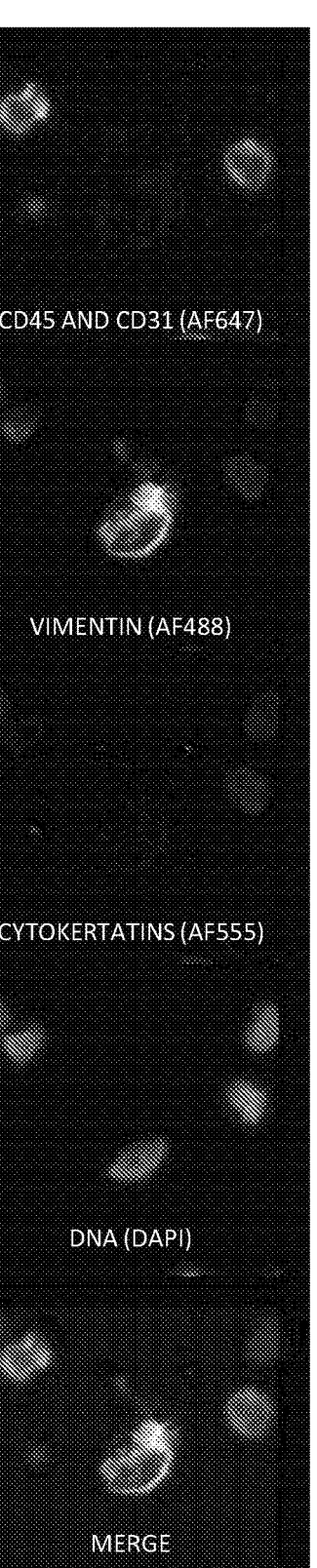
Figure 14:
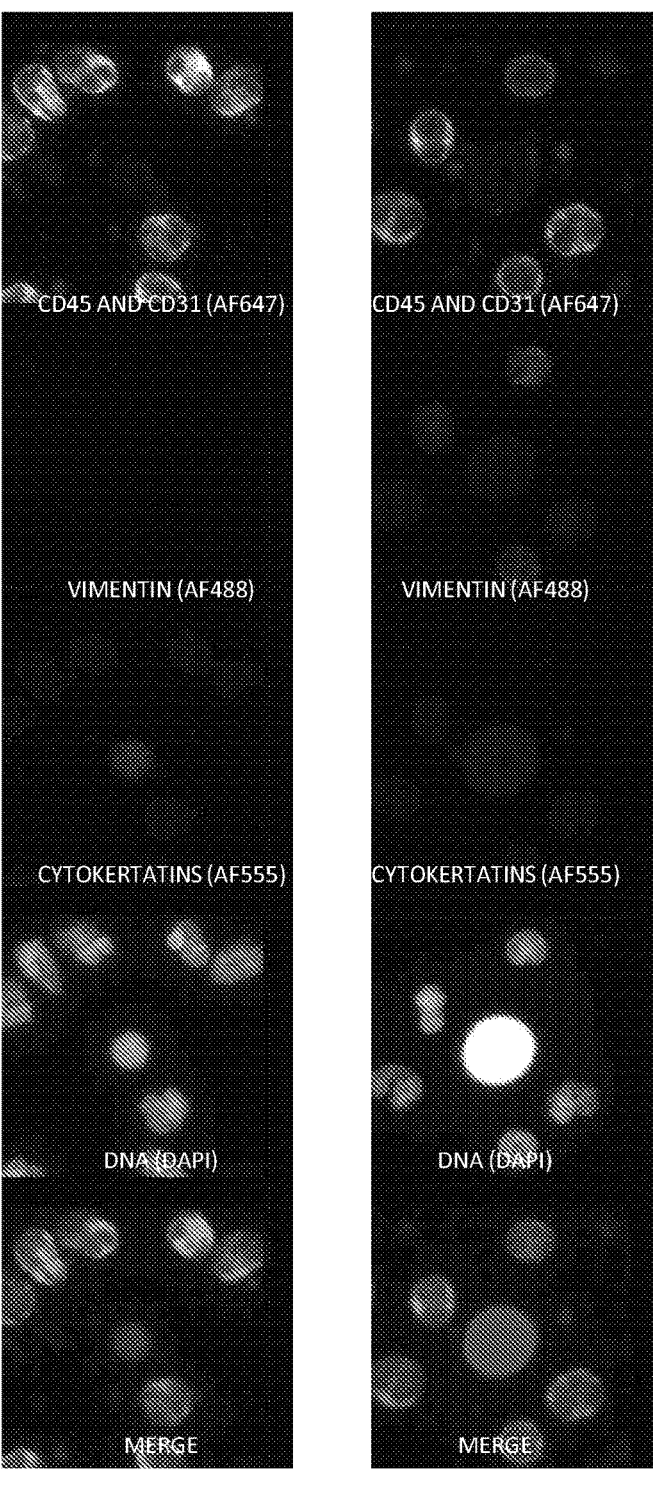
FIG. 14. Cells (DAPI+) negative for CD45, CD31, CK and vimentin.
Figure 15:
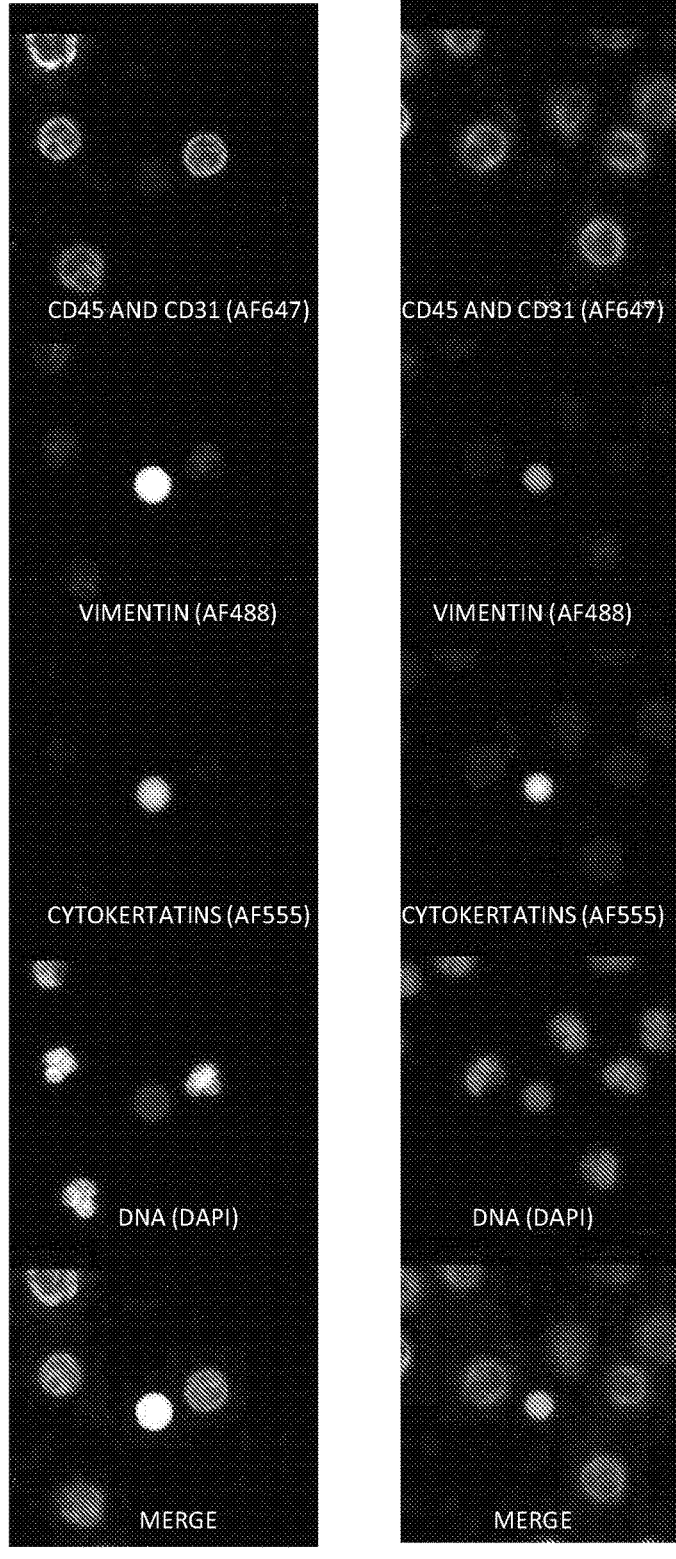
FIG. 15. Extra-cellular vesicles.
Figure 16:
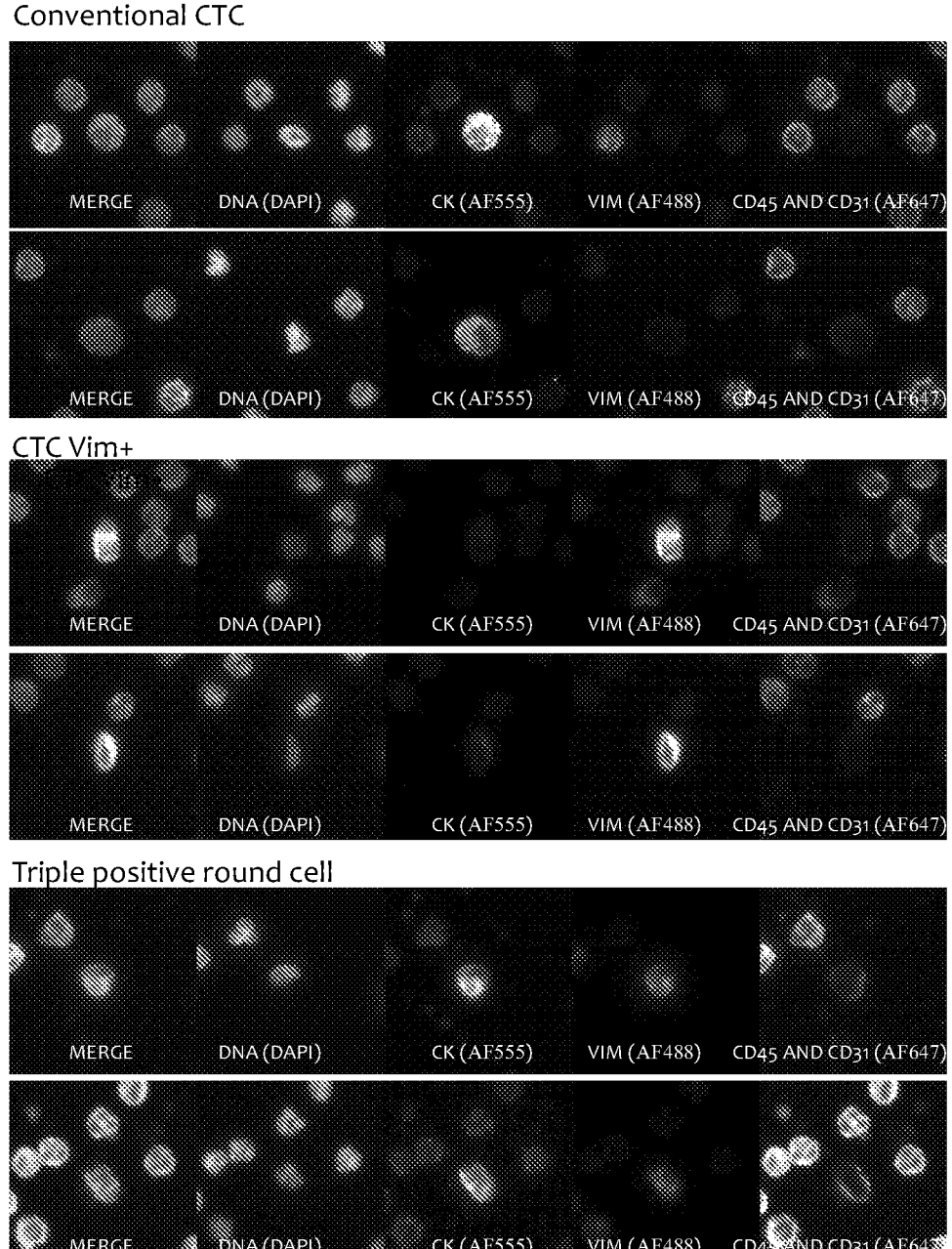
FIG. 16. An example of fluorescence and morphology micrographs of a patient generated by using an exemplary biological structure identification system of this disclosure. The patient has a metastatic prostate cancer. The liquid biopsy sample is a blood sample taken from the patient.
Figure 17:
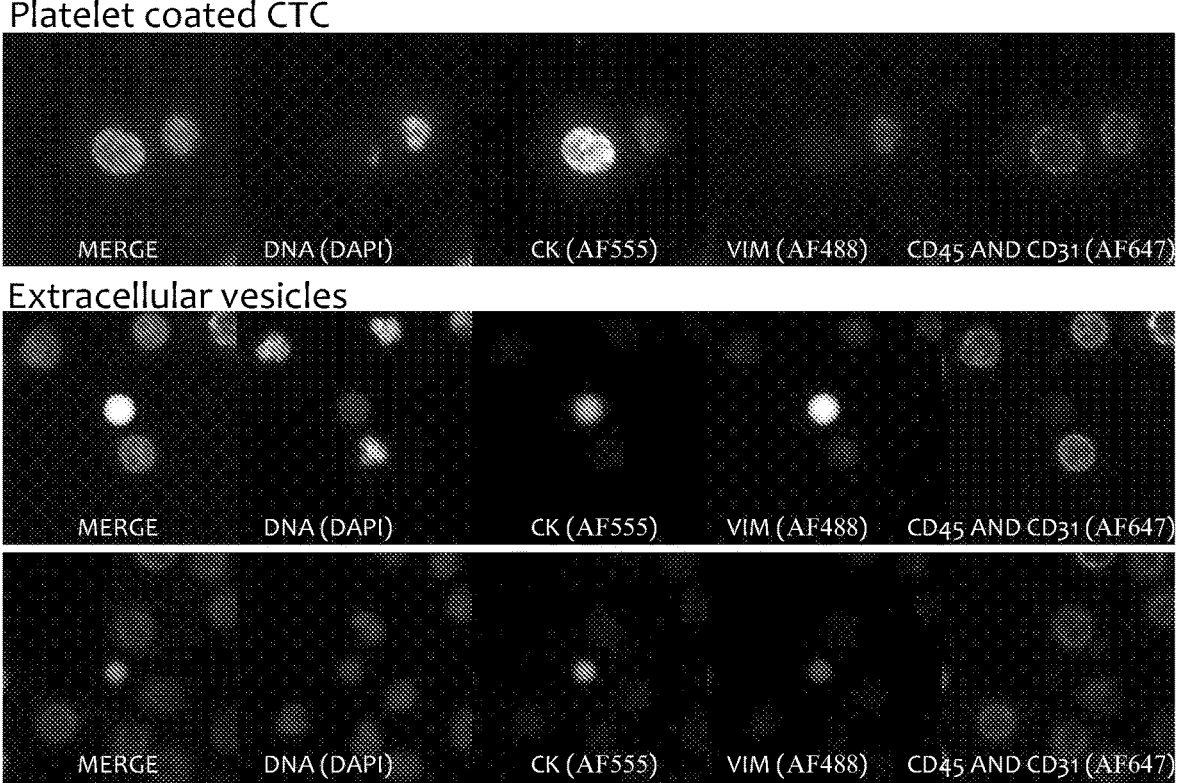
FIG. 17. An example of fluorescence and morphology micrographs of a patient generated by using an exemplary biological structure identification system of this disclosure. The patient has a metastatic prostate cancer. The liquid biopsy samples are a blood sample and a bone marrow sample taken from the patient.
Figure 17:
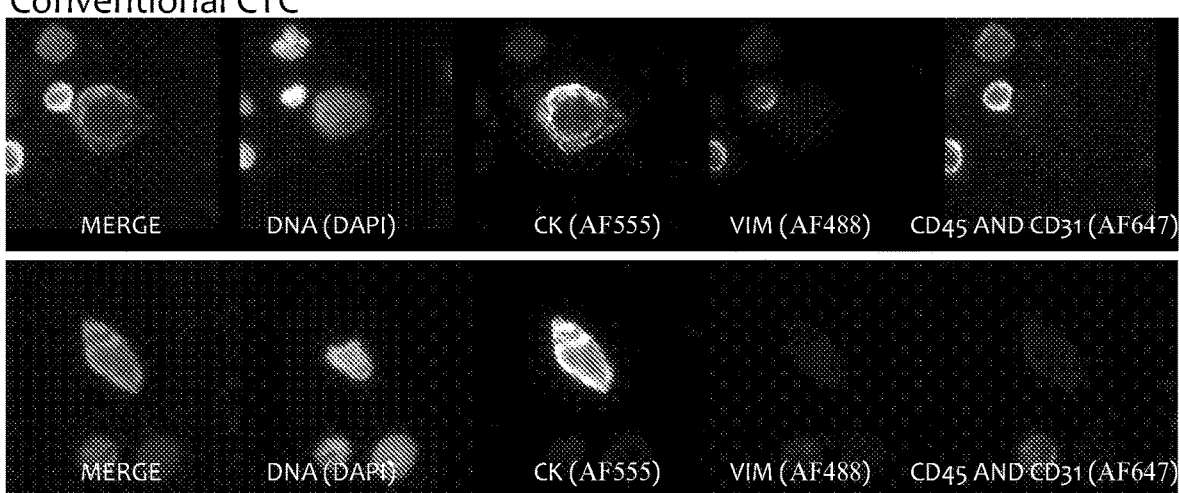
Figure 18:
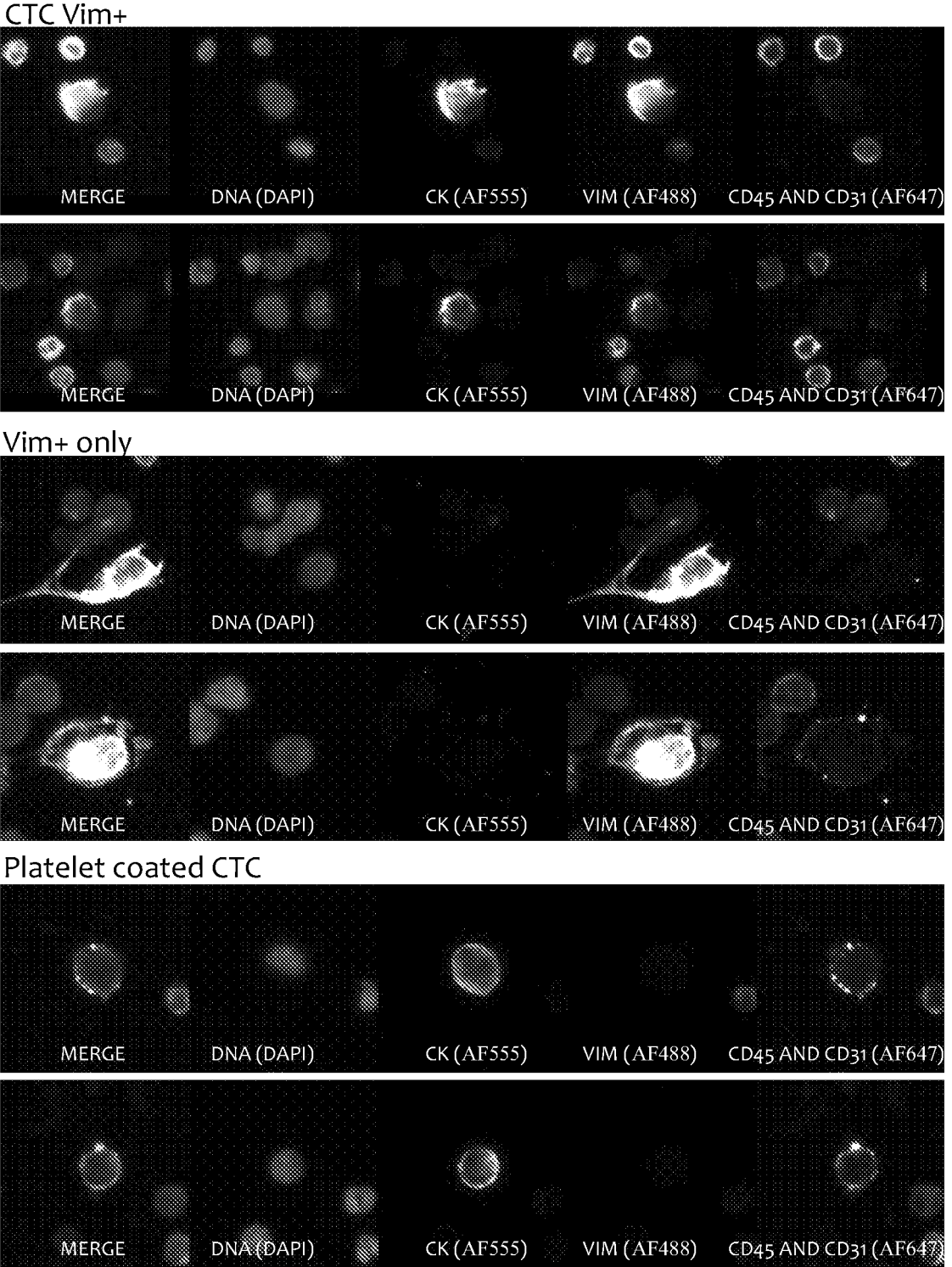
FIG. 18. An example of fluorescence and morphology micrographs of a patient generated by using an exemplary biological structure identification system of this disclosure.
Figure 19:
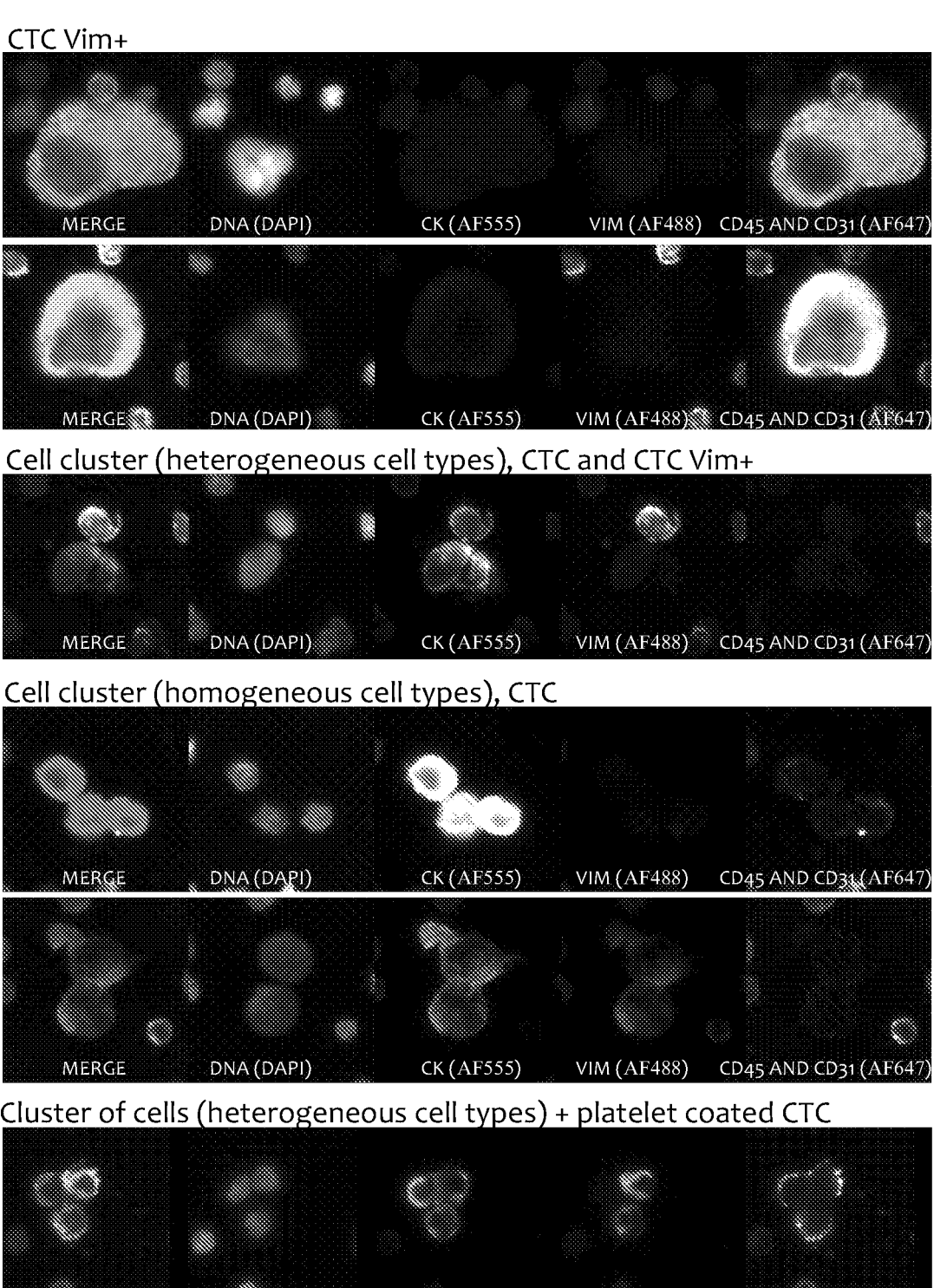
FIG. 19. An example of fluorescence and morphology micrographs of a patient generated by using an exemplary biological structure identification system of this disclosure.
Figure 20:
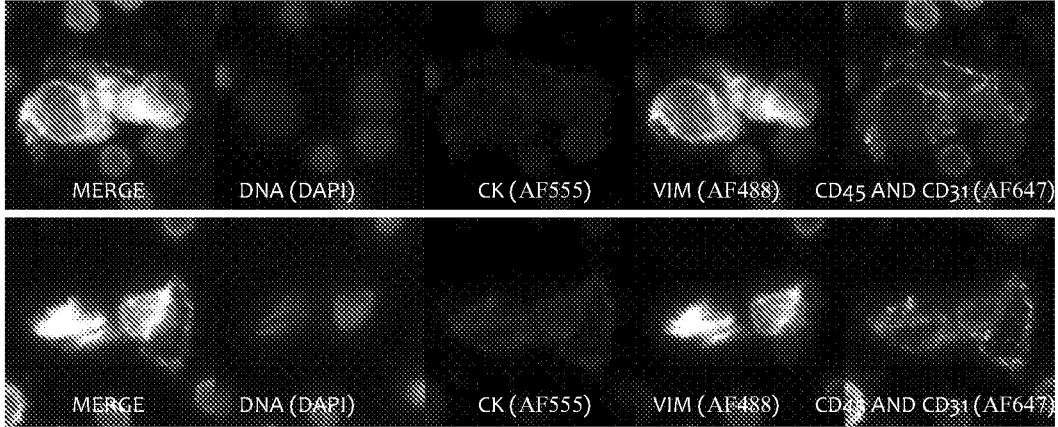
FIG. 20. An example of fluorescence and morphology micrographs of a patient generated by using an exemplary biological structure identification system of this disclosure. The patient has a Stage I non-small cell lung cancer (NSCLC). The liquid biopsy sample is a blood sample taken from the patient.
Figure 20:
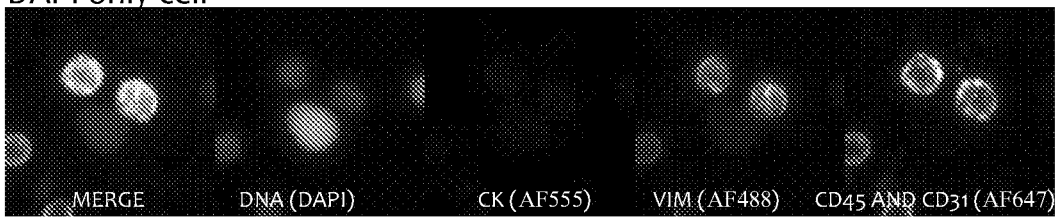
Figure 20:
Figure 21:
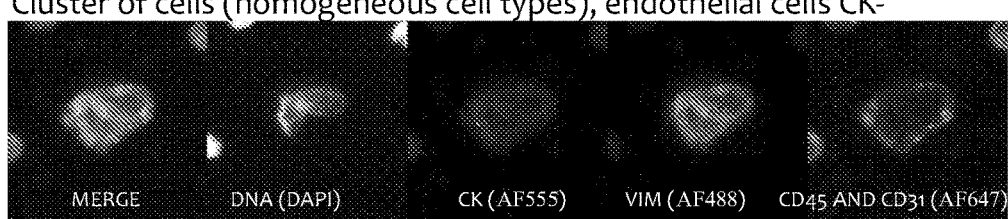
FIG. 21. An example of fluorescence and morphology micrographs of a patient generated by using an exemplary biological structure identification system of this disclosure. The patient has a Stage I non-small cell lung cancer (NSCLC). The liquid biopsy sample is a blood sample taken from the patient.
Figure 21:
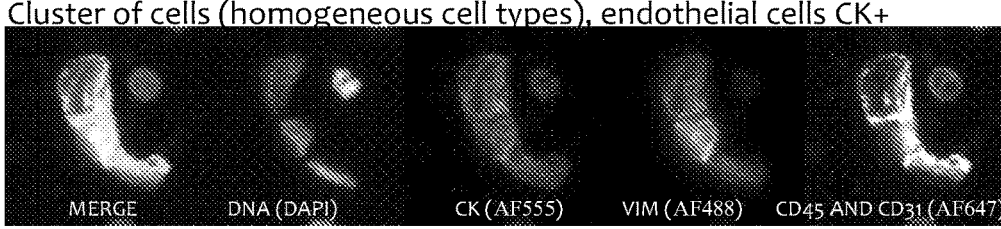
Figure 22:
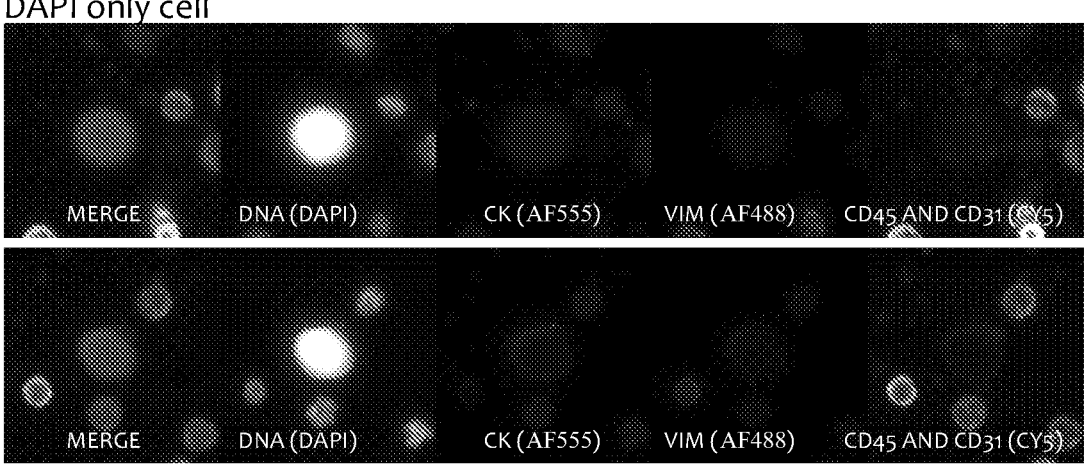
FIG. 22. An example of fluorescence and morphology micrographs of a patient generated by using an exemplary biological structure identification system of this disclosure.
Figure 23:
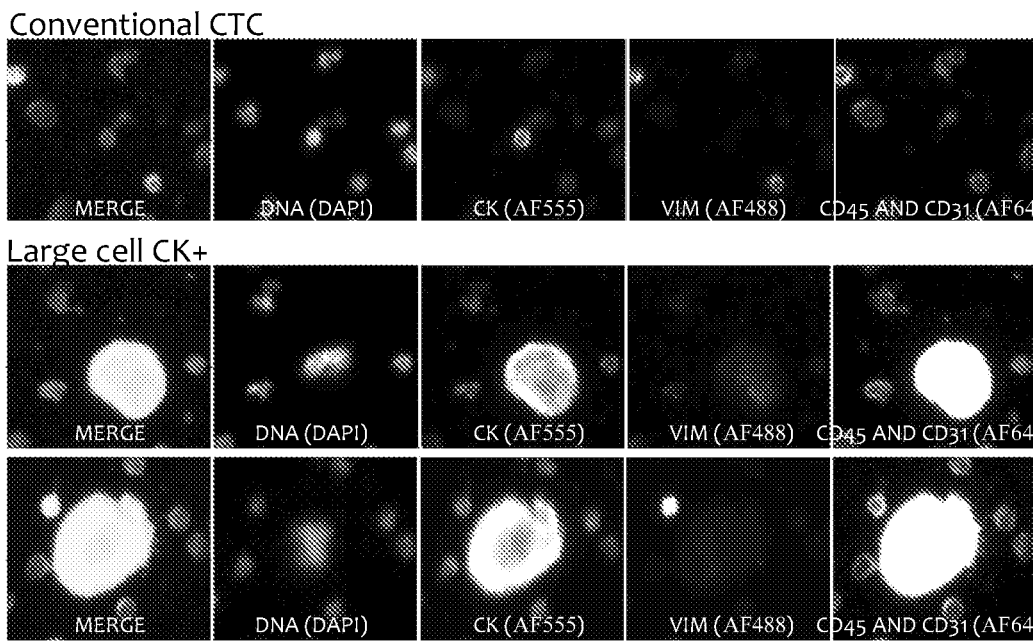
FIG. 23. An example of fluorescence and morphology micrographs of a patient generated by using an exemplary biological structure identification system of this disclosure. The patient has a prostate cancer. The liquid biopsy sample is a bone marrow sample taken from the patient.
Figure 24:
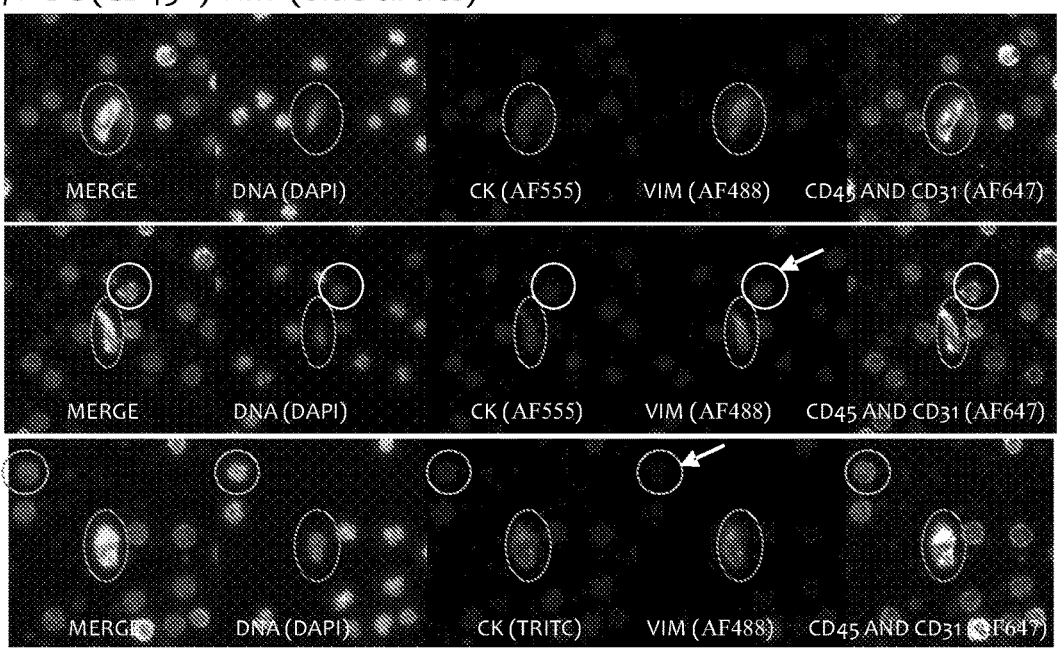
FIG. 24. An example of fluorescence and morphology micrographs of a patient generated by using an exemplary biological structure identification system of this disclosure.

In some aspects, a method of diagnosing a disease afflicting a patient is provided. This method may include having a liquid biopsy sample from the patient comprising biological structures; preparing a sample comprising a single layer of biological structures ("single biological structure layer sample") from the liquid biopsy sample; staining the biological structures of the single biological structure layer sample with a fluorescence assay (e.g., immunofluorescence assay such as the Baseline assay set forth herein or any fluorescent assay); applying (e.g., determining) the biological structure identification system(s) of this disclosure; identifying the rare biological structures through their fluorescence and morphology; forming a biological structure identification bucket ("identification bucket") based on the identified biological structure type, wherein each biological structure identification bucket contains the biological structure(s) that are similar in type; forming a set of identification buckets ("identification bucket set") based on the identification buckets; comparing information related to the identification bucket set to that of the atlas; determining the disease afflicting the patient; and treating the patient. FIGS. 5 and 6 illustrates the exemplary patient treatment methods of this disclosure.

FIG. 5 provides a flow chart exemplifying a method for treating a patient with the methods provided herein. A human with a disease is presented for evaluation (Box 300). A liquid biopsy sample is obtained from the patient (Box 310). As depicted by Box 320, a single layer biological structure sample is prepared. The Baseline assay is used to stain the single layer biological structure sample (Box 330). The sample is loaded into the biological structure identification system (Box 340). As depicted in Box 350, fluorescence and morphology of biological structures are detected and determined. Common biological structures and rare biological structures are placed into identification buckets as described above (Box 360). Identification bucket sets are formed from identification buckets (Box 370). A disease map is formed from identification bucket sets (Box 370). A disease atlas is queried (Box 390). From the query results, a disease and/or its stage can be diagnosed (Box 400). The human patient can then be treated based on this diagnosis (Box 410).

FIG. 6 provides another flow chart exemplifying a method for treating a patient with the methods provided herein. A human with a disease is presented for evaluation (Box 500). A liquid biopsy sample is obtained from the patient (Box 510). As depicted by Box 520, a single layer biological structure sample is prepared. The Baseline assay is used to stain the single layer biological structure sample (Box 530). The sample is loaded into the biological structure identification system (Box 540). As depicted in Box 550, fluorescence and morphology of biological structures are detected and determined. Identification buckets are created as described above (Box 560). The identification buckets are segregated into buckets for DAPI+ biological structures (Box 570) and buckets for DAPI-biological structures (Box 580). The buckets for DAPI+ biological structures can be further segregated into buckets for common cells (590) and buckets for rare cells (600). The bucket for DAPI– biological structures can be segregated into bucket for vesicles (Box 610). As depicted by Box 620, identification bucket sets of common and rare biological structures are created. A disease map is formed from identification bucket sets (Box 630). A disease atlas is queried (Box 640). From the query results, a disease and/or its stage can be diagnosed (Box 650). The human patient can then be treated based on this diagnosis (Box 660).

In the disease setting, in addition to these common immune cells, the liquid biopsy sample may further comprise rare cells that may actively escape or passively leak into the circulation and travel through the circulation, and may represent the disease.

Rare cells are defined as cells that are statistically distinct by their image analysis features. These rare cells are extracted by the following criteria: (a) after performing a bucketing analysis, the cells within the smallest population buckets are classified as rare; and (b) the cells within the cluster that is statistically deviant from the median value of all features from all cells are also classified as rare. The population of the rare cells may be lower than 5% of the total number of cells identified in the liquid biopsy sample. The population of the rare cells may be lower than 1% of the total number of cells identified in the liquid biopsy sample. The population of the rare cells may be lower than 0.1% of the total number of cells identified in the liquid biopsy sample.

The travel of the rare cells through the circulation may be with short half-lives or long half-lives. The rare cell travel may also include stopovers in various tissues along the way.

Representing the disease may mean that these rare cells may be (a) cancer cells as may be evidenced by their cancer genomic profiles and/or cancer protein markers; (b) tumor microenvironment cells that leak into circulation, wherein these cells may comprise epithelial cells, endothelial cells, mesenchymal cells, other stromal cells, cells that are in various transitional states, or a mixture thereof; (c) immune cells that may be responding to the tumor itself or cancer treatment; or (d) a mixture thereof.

The appearances of categories and classification of rare cells may be different across different cancers and stages of each cancer. Systems, methods and assays of this disclosure may identify various cellular subtypes both reproducibly for clinical practice while also enabling discovery of the unknown with an ability to detect a vast majority that have been implicated simultaneously in a unified experiment.

The subclasses of cells may be separated by protein and nuclear patterns as well as by cell morphology. The subclasses may be validated by downstream genomic or proteomic analyses, which might or might not be necessary for future clinical applications.

In another variation, one example relates to an approach to distinguish a substantially larger number of cellular groups using five markers. These markers are fluorescently protein antibodies or molecules labeled to four distinct fluorophores or fluorescent antibody. The computational method combines morphological differences as revealed by distinct fluorescence signatures to distinguish between at least twelve different rare cell subtypes, which may be present in the liquid biopsy sample. These rare cells are listed below.

This approach leverages both a new sample processing protocol reducing the five markers into four fluorescence channels and a novel computational method for classifying the different rare cells types via analysis of fluorescent microscopy images. Important for the success of this approach is the choice of marker combinations within and across fluorescent channels.

The computational approach is distinct from what everyone else is doing by putting 'every event' into a bucket of similar biological structures. Others look for specifics, for the known, which is a fundamental limitation of standard image analysis and of machine learning approaches as these would always ever only find the known. If on the other hand we force the computational method to accommodate every event on the slide defined by the existence of an imaging signal (in our current case it is fluorescent but it could also be brightfield), we can now cluster all events. As a next step, we allow for both common event clusters and rare event clusters. We in fact do not necessarily argue that all 'cancer events' are in rare clusters but instead we are effectively reducing the dimensionality of the total slide of millions of events with in itself hundreds of potential parameters, to a clustered framework that accommodates common (high frequency) and rare (low frequency) events. We know from the traditional CTC world that CTCs and by extension other disease associated events are typically rare.

The following examples illustrate the various embodiments of the present invention. Those skilled in the art will recognize many variations that are within the spirit of the present invention and scope of the claims.

Fluorescence and morphology micrographs generated by using the system of this disclosure from the liquid biopsy samples taken from patients are shown in FIGS. 7 to 24. The follow examples provide additional details for obtaining such micrographs.

Example 1. Examples of Rare Events

Examples of the rare cells, which may be present in the liquid biopsy, may be:

a. conventional circulating tumor cells (CK+/vimentin–/CD31–/CD45–);

b. circulating tumor cells (CK+/CD31–/CD45–) that do express vimentin, wherein tumor cells may putatively in epithelial to mesenchymal transition;

c. tumor cells (CK+) coated with platelets (CD31+);

d. endothelial cells (CD31+/vimentin+) that do not express CK;

e. endothelial cells (CD31+/vimentin+) that express CK;

f. megakaryocytes (CD31+) that do not express vimentin, wherein megakaryocytes may comprise large cell containing a single, large, multi-lobulated, polyploidy nucleus responsible for the production of blood thrombocytes platelets;

g. large cells that express CD31 (e.g. CD31+) and cytokeratins, (e.g. CK+), wherein these large cells may be present in the liquid biopsy samples obtained from a bone marrow;

h. cells (DAPI+) that express only vimentin;

i. round cells that express CD45 and CK (e.g. CD45+/CK+)

j. round cells that express CD45, vimentin and CK (e.g. CD45+/vimentin+/CK+)

k. clusters of cells ("cell cluster") comprising at least two cells, wherein the cells comprise same type of cells or different types of cells;

l. cells (DAPI+) that do not express, i.e. negative for CD45, CD31, CK and vimentin;

m. immune cells (CD45+) that do not express vimentin;

n. immune cells (CD45+) that express vimentin (type III intermediate filament protein), o. extra-cellular vesicles, or p. a mixture thereof.

Presence of each or combination of these rare cells in the liquid biopsy sample may be related to a cancer or indicative of presence of a cancer afflicting a living bod.

Example 2. Baseline Assay Protocol

A previously known set of antibodies against cytokeratin (CK), vimentin, CD31 and CD45 are used to develop an immunofluorescence assay that leverages both protein expression through these markers and cellular morphology at the appropriate resolution by fluorescence microscopic imaging. The use of these specific markers, which are allocated across three fluorescence channels while reserving the fourth channel for DAPI as a nuclear marker as described below, enables the Baseline assay protocol to differentiate a significant number of the rare cells as described above.

We allocate (a) the first immunofluorescence channel to the fluorescent dye, DAPI, for nuclear segmentation and characterization; (b) a second channel to cytokeratins for epithelial-like phenotype; (c) a third channel to vimentin, a type III intermediate filament protein for endothelial/mesenchymal-like phenotype; and (d) the fourth channel to both CD31 for endothelial-like phenotype and CD45 for immune cell phenotype.

Based on the understanding of differential cell morphologies, differential marker expressions, differential cellular distributions, and differential marker specificity/sensitivity requirements; the four fluorescence channels may be used, in one example, in the following way:

(i) a first channel: DNA/RNA labels (ii) a second channel: cytokeratins (CK)

(iii) a third channel: vimentin (iv) a fourth channel: CD45 and/or CD31

In another example, the following fluorophores and color assignments may be used for the four fluorescence channels:

a. a first channel: to label DNA/RNA, a fluorophore, DAPI with a fluorescence emission maximum at a wavelength of about 461 nm may be used. This first channel may be assigned to a blue color ("DAPI" channel).

b. a second channel: to label cytokeratins (CK), a fluorophore, Alexa Fluor 555 with a fluorescence emission maximum at a wavelength of about 565 nm may be used. This fluorophore may be used with an anti-CK mixture and a secondary Alexa Fluor 555 fluorescent antibody. This second channel may be assigned to a red color ("TRITC channel").

c. a third channel: to label vimentins, a fluorophore Alexa Fluor 488 with a fluorescence emission maximum at a wavelength of about 519 nm may be used. This fluorophore may be used with a directly conjugated antibody vimentin. This third channel may be assigned to an orange color ("FITC channel").

d. a fourth channel: to label CD45 and/or CD31, a fluorophore Alexa Fluor 647 with a fluorescence emission maximum at a wavelength of about 665 nm may be used. This fluorophore may be used with a directly conjugated antibodies for CD45 and/or CD31. This fourth channel may be assigned to a green color ("Cy5" channel).

The endothelial cells and the immune cells, which may be present in the same liquid biopsy sample, may still be differentiated from each other based on their differences in morphologies, though these cells are identified by the same fluorescent green color channel. The endothelial cells comparatively have highly elongated morphologies, and the immune cells comparatively have more round morphologies. Thus, we may still separate them even if markers expressed in these phenotypes may be combined in one channel, i.e. the Cy5 channel. We may also accept a certain degree of uncertainty in the differentiation between endothelial cells and immune cells, as we may be more interested in broad averages, or average numbers of endothelial cells observed, for example, by the fluorescence spectroscopy.

The endothelial cells typically express high amounts of vimentin plus argument above of separating immune cells that express vimentin still holds even for this class.

Endothelial phenotypes may also express low levels of cytokeratin. Also, transitions of epithelial to mesenchymal cells may result in co-expression. We may now separate them by CK+/vimentin+/CD31−/CD45−.

The most conventional cancer cells may be CK+/vimentin−/CD31−/CD45−.

For that reason, this Baseline assay protocol may enable substantially complete differentiation of the rare cell types present in the liquid biopsy samples at a suitable precision and accuracy.

Example 3. Blood Processing Procedure

A liquid biopsy sample comprising a blood sample may be processed according to the following procedure.

1. Receiving Sample:

Blood will be received in Cell Free DNA tubes. (4 mL-10 mL)

Sample should be shipped/stored at ambient temperature.

Samples must be processed within 18-30 hrs. from the time of draw.

Remove sample from packaging and inspect tube (compare to any paperwork provided)

2. Plasma Collection:

Centrifuge blood tube at 2000 g for 10 minutes at room temperature.(10 min)

Transfer 4 mL of plasma (upper phase) into 2-2 mL Eppendorf tubes. (Be careful not to disturb the buffy coat!) (1 min)

Spin the Eppendorf tubes in the bench top centrifuge at 14000 RPM for 10 minutes at room temperature. (10 min)

Transfer 4 mL of supernatant into 4-1 mL Corning cryogenic vial (orange cap) and temporarily store at 4° C. until the barcode has been printed. (1 min)

Plasma is ultimately stored at −80° C. in the location designated by OncoScope. (1 min)

Add 4 mL of 1×PBS pH7.4 to the original blood tube to reestablish initial volume. (1 min)

Put blood tube on the rocker for 5 minutes to homogenize the blood. (5 min)

3. Red Blood Cell Lysis:

Visually inspect blood tube for any clots. Manually separate solid chunks from liquid sample using a pipette to the best of your ability. Discard the solid chunks. (1 min)

Take white blood cell count using the Hematology Analyzer and determine the volume of blood to be lysed to produce a total of 12-16 slides.

4. Calculating Volume of Blood required to isolate 3.5 million WBC/slide:

Do not lyse more than 8 mL of blood & only lyse whole volumes of blood (i.e. not 4.7 mL or 4.3 mL, instead lyse 5 mL)

$$(x \text{ mL blood} * WBC \text{ count[million]}/mL)/(3.5\text{[million]} \\ WBC/\text{slide})=y \text{ slides}$$

5. Calculating Volume to Re-Suspend the WBC Pellet:

Multiply the number of slides possible for the amount of blood lysed by 0.75 mL y slides*0.75 mL/slide=mL PBS to resuspend WBC pellet 3 min Make 1× Lysis buffer from 10× stock solution using ddH$_2$O. (Do NOT use PBS, lysis will not work!)

6. Calculating volume of 1× Lysis Buffer:

Multiply the volume of blood to by lyse by 5.

x mL blood*5 mL 10× Lysis buffer/1 mL blood=1× Lysis (1 min)

Adjust the pH of the 1× Lysis to 7.40±0.02 right before using. (Remake if not used within 30 minutes of initial preparation) (1 min)

Add 5 mL of 1× Lysis buffer per 1 mL blood to be lysed in a 50 mL Falcon tube. (1 min)

Add the blood to the Falcon tube from the previous step and rock the tube for 5 minutes. Lysed blood will look clear, dark red. (Prolonged lysis time may damage WBC and CTCs!)

***Note: During these 2× 5 min steps, wash your slides (5 min)

Centrifuge the lysed blood for 5 minutes at 800 g at room temperature.

Make sure there is a cell pellet before continuing to the next step. (5 min)

Use vacuum line and glass Pasteur pipette to vacuum off supernatant. It is crucial to make sure to get rid of as much lysed RBCs without disturbing the WBC pellet. Be very careful! DO NOT disturb the pellet because may result in loss of CTCs. (2 min)

7. Washing Slides:

Grab plastic coplin jars and fill with 1×PBS pH7.4 (Note: 8 slides fit in one plastic coplin jar) (1 min.)

Using a pencil, label the frosty area of the slide with patient ID. (1 min)

The goal is to wash off the protective blue coat without letting the slide dry out.

Take all slides and coplin jars over to the sink. Set water to luke warm water. (Note: the water pressure should not be highly pressurized)

The water should be luke warm with normal to medium water pressure.

Wash one slide until protective layer is completely gone.

Without letting the slide dry, transfer to coplin jar. (Note: once the blue layer has been washed off, be careful not to touch the active area.) Slides that dry may affect the binding of cells.

8. WBC/CTC Platting:

Re-suspend the cell pellet in 1 mL of 1×PBS pH7.4 by gently pipetting up and down until the solution is homogenous. (Avoid making bubbles) (1 min.)

Add the remaining volume of 1×PBS pH7.4 require based on your calculations and agitate gently to homogenize. (Do not let pellet sit too long as WBCs may clump together) (1 min)

Plate 750 µL of re-suspended cell solution drop-wise evenly across the active area of the slide. (5-20 min)

Carefully rock the slide to spread the cell solution evenly. The black borders are hydrophobic and will keep the solution in the well. (1 min)

Place slide in Immuno Stain Moisture Chambers and repeat for the remaining slides. 1 min Place slide chamber(s) in incubator set at 37° C. for 40 minutes for cell attachment. During the incubation step, ensure you have completed the following:

Register the tube in OncoScope (refer to page 5 "Registering Samples in OncoScope"). Retrieve box and cut labels.

Prepare 7% BSA pH7.40. If already prepared take out of the fridge to allow it reach room temperature.

Set slide dryer @ 37° C. 40 min

9. Drying Slides:

Decant cell solution off slides into a waste jar at −45° angle off the upper right corner of each slide and add 750 µL of 7% BSA on the corners of each slide and spread gently over active area. Incubate at room temperature for 5 minutes.

Decant the BSA solution off each slide and wipe off excess moisture from the bottom of each slide with a Kim Wipe. (5 min)

Hold the slide vertically and allow excess BSA to drip onto a paper towel. Take care not to touch the active area with anything. (5 min)

Place the slides on the slide dryer for 5 to 12 minutes or until the active area is dry. (Do NOT over-dry slides as this will cause cracks in the BSA surface and disturb the cells!) (5-12 min)

Take slides off the heat block and tape the coverslip over the active area. Attach the barcode to each slide on the opposite side of the active area. (Ensure barcode labels are cut to fit the width of the slide and does not overhand on either sides) (5-20 min)

Wrap each slide in one sheet of aluminum foil and label with patient friendly name and slide number. (5-10 min)

Place wrapped slides into small white freezer storage boxes previously labeled with tube barcode. (1 min)

Place boxes in designated freezer rack position at −80° C. until they are ready to be stained. (1 min)

Example 4. OCULAR Rare Cell Detection

The purpose of "OCULAR" computational (rare) cell classification is to both categorize cell types identified by the Baseline assay protocol through into the correct bucket and identify new cell types. Cellular information for all the rare cell types, and aggregate cellular information for common cell clusters may separately be maintained. This combined unbiased methodology allows for reproducible characterization of known cell types and detection of rarer cells and cell types from an HD-SCA slide. It also enables backward compatibility of still finding the previously detected proto-typical CTC cells. In this way, OCULAR results can be compared with previous HD-SCA results using previous analytic approaches for finding CTCs and the rare cell types. Due to the unsupervised nature, OCULAR is also insensitive to variance in scanner image results (i.e. variance in exposure/gain/focus/protocol).

The OCULAR method includes an integration of existing methods leading to improved cell nuclear shape masking and inclusion of all fluorescence channels for building cell masks yielding more accurate morphological and fluorescence feature extraction. In addition, potential extra-cellular vesicles containing no structured nuclear material may be detected and placed into a separate category.

OCULAR may use an unsupervised clustering approach to analyze over 700 features per cell to detect the rare cells collecting them into groups of similar rare cells. This approach is not stochastic, reproducing the same rare cells and groups on repeated runs on the same dataset. All features per rare event are stored in a relational database that is queryable from any application capable of accessing said database. The rare cell groups, common cell groups, and Dapi− event groups are stored in their aggregate form (the mean of each feature within that group) in an RDS file, which is a file format readable by R.

OCULAR may also contain a web-based method for presenting the results of the rare cell detection analysis to a trained user to quickly and easily verify or re-categorize cells in various rare cell groups. After enough confidence or a large enough HD-SCA sample size is analyzed, OCULAR may produce a dataset that will be reflective of any potential cell. In other words, any cell that OCULAR has seen may belong to a row in this dataset via similarity in data. This dataset, hereafter called as ATLAS, may effectively be a static dataset, and may only be updated when a new cell type is discovered. ATLAS may further be analyzed for discovery of novel cell types in circulation and to perform correlations and enumerations of cells and cell groups across patients and cancer types.

In addition, OCULAR methodology may be used with any fluorescent labeling approach that may be used DAPI to label the nucleus.

This assay protocol and computational approach may fully be compatible with existing fluorescence-based whole slide scanning methodologies and downstream single-cell genomic and proteomic analysis methods.

Each glass slide may have in the order of 3 million events that we can identify via imaging in four colors. The rare events, which identify the rare cells in about 3 million events may be in the range of less than 1 event in 1,000 events to 1 in 1,000,000. OCULAR approach may take each event and may ask if a similar event has already been seen on the slide given a set of image analysis parameters. If yes, this event may be put it in the same bucket/cluster; and if no, this event may be put it into a new bucket/cluster. Then, through OCULAR approach, a set number of common cell buckets (effectively representing the total repertoire of immune cells) and a set number of rare cell buckets are identified.

The common cell buckets may be used to describe the immune system state similar to a differential blood count. The rare cell buckets may be both unbiased and reproducible because the clustering algorithm is fixed. Then, we may have a 'hands-free' analysis pipeline that produces these rare buckets, which in turn give us the starting point for biological interpretation both within specific clinical intended use and across disease states.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A biological structure identification system comprising:

an optical imaging system configured to illuminate a liquid biopsy sample having one or more biological structures that are labeled with a fluorophore and to detect emitted electromagnetic radiation from the liquid biopsy sample as image data thereby generating images of biological structures;

an image detection system configured to detect images of the biological structures generated by the optical imaging system; and a processing system that communicates with the optical imaging system and the image detection system, wherein the processing system is configured to:

segment events into DAPI-positive (DAPI+) and DAPI-negative (DAPI–) events from images acquired using four fluorescence channels, wherein a first channel is assigned to DAPI for nuclear segmentation and characterization, a second channel to cytokeratin (CK), a third channel to vimentin, and a fourth channel simultaneously to CD31 and CD45, where DAPI means 4',6-diamidino-2-phenylindole.;

determine a plurality of high-dimensional features of the biological structures related to fluorescence and morphological descriptors, wherein a plurality of features are determined from the images;

transform the plurality of features with principal component analysis (PCA) to PCA-transformed features and performing hierarchical clustering on a distance matrix of the PCA-transformed features;

form biological structure identification buckets ("identification buckets") from the plurality of features, each biological structure identification bucket identifying biological structures that are similar in type;

form a set of identification buckets ("identification bucket set") based on identification buckets for both DAPI+and DAPI-events, including extracellular vesicles detected in a DAPI-event stream; and generate an image of a disease map from identification bucket sets and identification buckets and configured for comparison to a disease atlas.

2. The biological structure identification system of claim 1, wherein the one or more biological structures include one or more rare biological structures.

3. The biological structure identification system of claim 1, wherein the one or more biological structures include a simultaneously identified multiple biological structures.

4. The biological structure identification system of claim 1, wherein the optical imaging system includes:

a liquid biopsy sample carrier suitable for receiving supporting the liquid biopsy sample;

an illumination system capable of illuminating the liquid biopsy sample at a specific wavelength or wavelengths that can be absorbed by the fluorophore;

a light detection system configured to detect and determine an intensity and a wavelength of fluorescence emitted by the fluorophore; and a light controlling system configured to allow detection of emitted electromagnetic radiation from the liquid biopsy sample; allow detection of electromagnetic radiation scattered by, reflected by, and/or transmitted through the liquid biopsy sample; and guide electromagnetic radiation from the illumination system to the liquid biopsy sample, and from the liquid biopsy sample to the light detection system.

5. The biological structure identification system of claim 1 wherein at least a subset of the one or more biological structures includes a component selected from the group consisting of a structure with a membrane, a protein, DNA, RNA, and combinations thereof.

6. The biological structure identification system of claim 1 wherein at least a subset of the one or more biological structures is a structure with a membrane selected from the group consisting of a cell, a vesicle, and combinations thereof.

7. The biological structure identification system of claim 6 wherein the vesicle is an oncosome.

8. The biological structure identification system of claim 6 wherein the vesicle is an oncosome that has a characteristic size equal to or larger than one micrometer.

9. The biological structure identification system of claim 6 wherein the vesicle is an oncosome that has a characteristic size larger than exosome.

10. The biological structure identification system of claim 1 wherein the liquid biopsy sample is a non-solid biological sample.

11. The biological structure identification system of claim 1 wherein the liquid biopsy sample is a body fluid sample.

12. The biological structure identification system of claim 1 wherein the liquid biopsy sample comprises a blood sample, a bone marrow sample, a peritoneal fluid sample, a urine sample, a saliva, a vaginal fluid sample, a semen sample, a tear sample, a mucus sample, an aqueous humor sample, cerebrospinal fluid (CSF) sample, or a combination thereof.

13. The biological structure identification system of claim 1 wherein the liquid biopsy sample comprises a blood sample.

14. The biological structure identification system of claim 1 wherein the liquid biopsy sample comprises common immune cells and rare biological structures.

15. The biological structure identification system of claim 14 wherein the rare biological structures are:

cancer cells that have cancer genomic profiles and/or cancer protein markers;

tumor microenvironment cells that leak into circulation, wherein these cells comprise epithelial cells, endothelial cells, mesenchymal cells, other stromal cells, cells that are in various transitional states, or a mixture thereof;

immune cells that are responding to a tumor itself or cancer treatment;

vesicles; or mixtures thereof.

16. The biological structure identification system of claim 14 wherein the rare biological structures comprise:

conventional circulating tumor cells, which are CK+, vimentin–, CD31– and CD45–;

circulating tumor cells, which are CK+, CD31–, CD45–, and vimentin+, and wherein tumor cells may putatively in epithelial to mesenchymal transition;

tumor cells, which are CK+, and coated with platelets, which are CD31+;

endothelial cells, which are CD31+, vimentin+, and CK–;

endothelial cells, which are CD31+, vimentin+ and CK+;

megakaryocytes, which are CD31+ and vimentin–, wherein megakaryocytes include large cells containing a single, large, multi-lobulated, polyploidy nucleus responsible for production of blood thrombocytes platelets;

large cells, which are CD31+ and CK+, wherein these large cells may be present in liquid biopsy samples obtained from a bone marrow;

cells, which are DAPI+ and vimentin+;

round cells, which are CD45+ and CK+;

round cells, which are CD45+, vimentin+, and CK+;

clusters of cells ("cell cluster") comprising at least two cells, wherein the cells are same type of cells and/or different types of cells;

cells, which are DAPI+, CD45−, CD31−, and CK−;

immune cells, which are CD45+ and vimentin−;

immune cells, which are CD45+ and vimentin+(type III intermediate filament protein), extra-cellular vesicles; or a mixture thereof.

17. The biological structure identification system of claim 1, wherein the liquid biopsy sample comprises common biological structures and rare biological structures such that a total number of biological structures being a sum of number of common biological structures and rare biological structures, and wherein the rare biological structures are present in an amount equal to or less than 10%, 5%, 1%, 0.1%, or 0.01% of the total number of biological structures.

18. The biological structure identification system of claim 1, wherein the emitted electromagnetic radiation is a fluorescent radiation.

19. The biological structure identification system of claim 1 wherein, wherein the optical imaging system comprises an excitation filter, an emission filter, a dichroic mirror, a lens, an optical fiber, or a combination thereof.

20. The biological structure identification system of claim 1 wherein the optical imaging system comprises a fluorescence microscope, a brightfield microscope, or a combination thereof.

21. The biological structure identification system of claim 1 wherein the processing system comprises a control system, a hardware processor, a memory system, and an information conveying system.

22. The biological structure identification system of claim 20 wherein the biological structure identification system has 4 of 7 fluorescence channels.

23. The biological structure identification system of claim 1, wherein the biological structure identification system has only four fluorescence channels.

24. The biological structure identification system of claim 1, wherein the biological structure identification system has only four fluorescence channels, wherein the four fluorescence channels are:

a first fluorescence channel configured for detection of fluorescence emission at a blue color wavelength region;

a second fluorescence channel configured for detection of fluorescence emission at a red color wavelength region;

a third fluorescence channel configured for detection of fluorescence emission at an orange color wavelength region; and a fourth fluorescence channel configured for detection of fluorescence emission at a green color wavelength region.

25. The biological structure identification system of claim 24, wherein the biological structure identification system has only four fluorescence channels and is configured to identify endothelial cells and immune cells from the plurality of features.

26. The biological structure identification system of claim 25 wherein the biological structure identification system has only four fluorescence channels and is configured to identify the endothelial cells and the immune cells from the plurality of features, and to differentiate the endothelial cells from the immune cells, wherein the endothelial cells have more elongated morphologies as compared to the immune cells, and the immune cells have more round morphologies as compared to the endothelial cells.

27. The biological structure identification system of claim 1, wherein a biological structure's morphology is determined from at least 10 features, at least 100 features, from the images or the image data.

28. The biological structure identification system of claim 27, wherein at least a subset of the features are related to size, shape, texture and structure of the one or more biological structures.

29. The biological structure identification system of claim 1, wherein the liquid biopsy sample is obtained from a diseased human.

30. The biological structure identification system of claim 1, wherein the liquid biopsy sample is obtained from a human afflicted with a cancer.

31. The biological structure identification system of claim 1, wherein processing system is further configured to form a disease map based on information related to one or more biological structure identification bucket sets, relate the disease map to a specific disease and disease stage, and label the disease map according to an identified related specific disease and disease stage.

32. The biological structure identification system of claim 31, wherein the biological structure identification system is further configured to store a disease map based on information related to one or more identification bucket sets and labeled by disease type and disease stage, and wherein a disease afflicting a subject causes formation of the biological structures forming the one or more identification bucket sets.

33. The biological structure identification system of claim 1, wherein the biological structure identification system is configured to form disease maps of at least two different disease types and disease stages.

34. The biological structure identification system of claim 1, wherein the biological structure identification system is further configured to form a disease atlas of disease maps from disease maps of different disease types and disease stages.

35. The biological structure identification system of claim 1, wherein the biological structure identification system is further configured to diagnose a disease type and its stage based on a received liquid biopsy sample from a human afflicted with a disease.

36. The biological structure identification system of claim 1, wherein the biological structure identification system is further configured to diagnose a disease type and its stage based on the liquid biopsy sample received from a human afflicted with a disease by comparing a disease map formed for a received liquid biopsy sample with the disease maps of the disease atlas stored in the biological structure identification system prior to receiving the liquid biopsy sample.

37. The biological structure identification system of claim 1, wherein the biological structure identification system further comprises an information conveying system that is configured to convey to a user information related to types of the biological structures present in the liquid biopsy sample, biological structure identification buckets, disease maps, disease atlases, or a combination thereof.

38. A method of analyzing a liquid biopsy sample, comprising:

receiving the liquid biopsy sample comprising biological structures;

preparing a sample comprising a single layer biological structure sample from the liquid biopsy sample, the single layer biological structure sample including a single layer of biological structures;

staining the biological structures of the single layer biological structure sample with a fluorescence assay; and analyzing the sample with a biological structure identification system configured to:

segment events into DAPI-positive (DAPI+) and DAPI-negative (DAPI−) events from images acquired using four fluorescence channels, wherein a first channel is assigned to DAPI for nuclear segmentation and characterization, a second channel to cytokeratin (CK), a third channel to vimentin, and a fourth channel simultaneously to CD31 and CD45, where DAPI means 4',6-diamidino- 2-phenylindole,;

determine a plurality of high-dimensional features of the biological structures related to fluorescence and morphological descriptors, wherein a plurality of features are determined from the images;

transform the plurality of features with principal component analysis (PCA) to PCA-transformed features and performing hierarchical clustering on a distance matrix of the PCA-transformed features;

form biological structure identification buckets ("identification buckets") from the plurality of features, each biological structure identification bucket identifying biological structures that are similar in type;

form a set of identification buckets ("identification bucket set") based on identification buckets for both DAPI+ and DAPI−events, including extracellular vesicles detected in a DAPI-event stream; and generate an image of a disease map from identification bucket sets and identification buckets and configured for comparison to a disease atlas.

39. A method of diagnosing a disease using the biological structure identification system of claim 1 comprising:

receiving a liquid biopsy sample from a patient comprising biological structures;

preparing a sample comprising a single biological structure layer sample from the liquid biopsy sample, the single biological structure layer sample being a single layer of biological structures;

staining the biological structures of the single layer biological structure sample with a fluorescence assay; and analyzing the sample with a biological structure identification system configured to: and segment events into DAPI-positive (DAPI+) and DAPI-negative (DAPI−) events from images acquired using four fluorescence channels, wherein a first channel is assigned to DAPI for nuclear segmentation and characterization, a second channel to cytokeratin (CK), a third channel to vimentin, and a fourth channel simultaneously to CD31 and CD45, where DAPI means 4',6-diamidino- 2-phenylindole.;

determine a plurality of high-dimensional features of the biological structures related to fluorescence and morphological descriptors, wherein a plurality of features are determined from the images;

transform the plurality of features with principal component analysis (PCA) to PCA-transformed features and performing hierarchical clustering on a distance matrix of the PCA-transformed features;

form biological structure identification buckets ("identification buckets") from the plurality of features, each biological structure identification bucket identifying biological structures that are similar in type;

form a set of identification buckets ("identification bucket set") based on identification buckets for both DAPI+ and DAPI−events, including extracellular vesicles detected in a DAPI-event stream; and generate an image of a disease map from identification bucket sets and identification buckets and configured for comparison to a disease atlas; and treating the patient.

\* \* \* \* \*